(12) United States Patent
Forsell

(10) Patent No.: US 9,649,194 B2
(45) Date of Patent: May 16, 2017

(54) HIP JOINT DEVICE

(76) Inventor: Peter Forsell, Bouveret (CH)

( * ) Notice: Subject to any disclaimer, the term of this patent is extended or adjusted under 35 U.S.C. 154(b) by 0 days.

(21) Appl. No.: 13/382,678

(22) PCT Filed: Jul. 12, 2010

(86) PCT No.: PCT/SE2010/050802
§ 371 (c)(1),
(2), (4) Date: Jan. 6, 2012

(87) PCT Pub. No.: WO2011/005186
PCT Pub. Date: Jan. 13, 2011

(65) Prior Publication Data
US 2012/0109327 A1    May 3, 2012

Related U.S. Application Data

(60) Provisional application No. 61/229,738, filed on Jul. 30, 2009, provisional application No. 61/229,755, (Continued)

(30) Foreign Application Priority Data

Jul. 10, 2009  (SE) ...................................... 0900957
Jul. 10, 2009  (SE) ...................................... 0900958
(Continued)

(51) Int. Cl.
*A61F 2/32*      (2006.01)
*A61F 2/34*      (2006.01)
(Continued)

(52) U.S. Cl.
CPC .............. *A61F 2/3609* (2013.01); *A61F 2/34* (2013.01); *A61F 2002/305* (2013.01);
(Continued)

(58) Field of Classification Search
CPC ..................................................... A61F 2/3609
(Continued)

(56) References Cited

U.S. PATENT DOCUMENTS 3,002,466 A * 10/1961 Read .............................. 417/456
3,003,399 A * 10/1961 Donner ....................... 89/37.13
(Continued)

FOREIGN PATENT DOCUMENTS

| DE | 102004008138 A1 | 9/2009 |
|---|---|---|
| FR | 2824259 A1 | 11/2002 |
| GB | 1302834 | 1/1973 |

OTHER PUBLICATIONS

International Search Report for PCT/SE2010/050802, mailed Oct. 25, 2010.

*Primary Examiner* — Alvin Stewart

(57) ABSTRACT

A medical device for implantation in a hip joint of a patient is provided. The hip joint has a caput femur integrated with a collum femur having a collum and caput center axis, extending longitudinal along the collum and caput femur, in the center thereof. The medical device comprises an elongated portion adapted to at least partially replace the collum femur. The elongated portion is adapted to be connected to a prosthetic spherical portion adapted to replace the caput femur. The prosthetic spherical portion in turn is adapted to be movably placed in a prosthetic replacement for the acetabulum comprising at least one extending portion adapted to clasp said prosthetic spherical portion. The elongated portion comprises a restricting portion adapted to restrict the motion range of the spherical portion in relation to said prosthetic replacement for the acetabulum. The restricting portion of the elongated portion is adapted to enable an advantageous motion range in relation to said prosthetic replacement for the acetabulum.

20 Claims, 32 Drawing Sheets

Related U.S. Application Data filed on Jul. 30, 2009, provisional application No. 61/229,739, filed on Jul. 30, 2009, provisional application No. 61/229,743, filed on Jul. 30, 2009, provisional application No. 61/229,745, filed on Jul. 30, 2009, provisional application No. 61/229,746, filed on Jul. 30, 2009, provisional application No. 61/229,747, filed on Jul. 30, 2009, provisional application No. 61/229,748, filed on Jul. 30, 2009, provisional application No. 61/229,751, filed on Jul. 30, 2009, provisional application No. 61/229,752, filed on Jul. 30, 2009, provisional application No. 61/229,761, filed on Jul. 30, 2009, provisional application No. 61/229,767, filed on Jul. 30, 2009, provisional application No. 61/229,778, filed on Jul. 30, 2009, provisional application No. 61/229,786, filed on Jul. 30, 2009, provisional application No. 61/229,789, filed on Jul. 30, 2009, provisional application No. 61/229,796, filed on Jul. 30, 2009, provisional application No. 61/229,735, filed on Jul. 30, 2009.

(30) Foreign Application Priority Data

| Jul. 10, 2009 | (SE) | 0900959 |
|---|---|---|
| Jul. 10, 2009 | (SE) | 0900960 |
| Jul. 10, 2009 | (SE) | 0900962 |
| Jul. 10, 2009 | (SE) | 0900963 |
| Jul. 10, 2009 | (SE) | 0900965 |
| Jul. 10, 2009 | (SE) | 0900966 |
| Jul. 10, 2009 | (SE) | 0900968 |
| Jul. 10, 2009 | (SE) | 0900969 |
| Jul. 10, 2009 | (SE) | 0900970 |
| Jul. 10, 2009 | (SE) | 0900972 |
| Jul. 10, 2009 | (SE) | 0900973 |
| Jul. 10, 2009 | (SE) | 0900974 |
| Jul. 10, 2009 | (SE) | 0900976 |
| Jul. 10, 2009 | (SE) | 0900978 |
| Jul. 10, 2009 | (SE) | 0900981 |

(51) Int. Cl.
  *A61F 2/36* (2006.01)
  *A61F 2/30* (2006.01)
  *A61F 2/46* (2006.01)

(52) U.S. Cl.
  CPC .......... *A61F 2002/30125* (2013.01); *A61F 2002/30153* (2013.01); *A61F 2002/30154* (2013.01); *A61F 2002/30166* (2013.01); *A61F 2002/30179* (2013.01); *A61F 2002/30364* (2013.01); *A61F 2002/30469* (2013.01); *A61F 2002/30471* (2013.01); *A61F 2002/3208* (2013.01); *A61F 2002/3443* (2013.01); *A61F 2002/3625* (2013.01); *A61F 2002/4631* (2013.01)

(58) Field of Classification Search
  USPC .......... 623/19.11–19.14, 22.14, 22.15, 623/21.16–21.17, 22.17, 22.46, 23.35, 623/22.3, 22.11, 22.43, 22.42
  See application file for complete search history.

(56) References Cited

U.S. PATENT DOCUMENTS

| 3,493,252 | A | * | 2/1970 | Watson et al. | 403/122 |
|---|---|---|---|---|---|
| 3,584,318 | A | * | 6/1971 | Scales et al. | A61F 2/32 |
| | | | | | 403/140 |
| 3,608,096 | A | * | 9/1971 | Link | A61F 2/34 |
| | | | | | 623/22.39 |
| 3,638,243 | A | * | 2/1972 | Campbell et al. | 623/20.22 |
| 3,656,184 | A | * | 4/1972 | Chambers | 623/22.15 |
| 3,795,922 | A | * | 3/1974 | Herbert et al. | 623/20.22 |
| 3,903,549 | A | * | 9/1975 | Deyerle | 623/22.36 |
| 3,918,102 | A | * | 11/1975 | Eichler | 623/22.39 |
| 3,982,281 | A | * | 9/1976 | Giliberty | 623/22.24 |
| 4,135,517 | A | * | 1/1979 | Reale | A61F 2/36 |
| | | | | | 606/86 R |
| 4,279,041 | A | * | 7/1981 | Buchholz | 623/19.12 |
| 4,524,467 | A | * | 6/1985 | DeCarlo, Jr. | A61F 2/32 |
| | | | | | 623/19.12 |
| 4,642,123 | A | * | 2/1987 | Noiles | A61F 2/32 |
| | | | | | 623/22.2 |
| 4,712,814 | A | * | 12/1987 | Petterson | 285/325 |
| 4,834,759 | A | * | 5/1989 | Spotorno et al. | 623/22.3 |
| 4,950,299 | A | * | 8/1990 | Noiles | A61F 2/32 |
| | | | | | 623/22.18 |
| 5,116,379 | A | * | 5/1992 | McLardy-Smith | 623/22.42 |
| 5,387,244 | A | * | 2/1995 | Breard | 623/23.15 |
| 5,507,819 | A | * | 4/1996 | Wolf | 623/19.11 |
| 5,549,681 | A | * | 8/1996 | Segmuller et al. | 623/23.4 |
| 5,549,697 | A | * | 8/1996 | Caldarise | 623/22.26 |
| 5,674,297 | A | * | 10/1997 | Lane et al. | 623/21.16 |
| 5,879,406 | A | * | 3/1999 | Lilley | 623/22.15 |
| 5,916,270 | A | * | 6/1999 | Lipman | 623/22.15 |
| 6,042,611 | A | * | 3/2000 | Noiles | 623/22.21 |
| 6,099,571 | A | * | 8/2000 | Knapp | 623/21.16 |
| 6,139,583 | A | * | 10/2000 | Johnson | 623/23.15 |
| 6,200,350 | B1 | * | 3/2001 | Masini | 623/23.15 |
| 6,238,436 | B1 | * | 5/2001 | Lob et al. | 623/22.42 |
| 6,352,560 | B1 | * | 3/2002 | Poeschmann et al. | 623/23.4 |
| 6,361,566 | B1 | * | 3/2002 | Al-Hafez | 623/22.15 |
| 6,413,280 | B1 | * | 7/2002 | Feiler | 623/22.15 |
| 6,423,097 | B2 | * | 7/2002 | Rauscher | A61F 2/4241 |
| | | | | | 623/21.15 |
| 6,454,808 | B1 | * | 9/2002 | Masada | A61F 2/4241 |
| | | | | | 623/21.13 |
| 6,607,560 | B1 | * | 8/2003 | Pfaff et al. | 623/22.45 |
| 6,620,200 | B1 | * | 9/2003 | Descamps | A61F 2/30771 |
| | | | | | 623/22.32 |
| 6,802,866 | B2 | * | 10/2004 | Bunz | 623/22.14 |
| 6,896,703 | B2 | * | 5/2005 | Barbieri et al. | 623/22.3 |
| 7,179,296 | B2 | * | 2/2007 | Dooney | 623/22.21 |
| 7,833,276 | B2 | * | 11/2010 | Auxepaules | A61F 2/32 |
| | | | | | 623/22.18 |
| 7,985,261 | B2 | * | 7/2011 | Masini | 623/23.11 |
| 8,029,572 | B2 | * | 10/2011 | McLean | 623/22.15 |
| 8,052,755 | B2 | * | 11/2011 | Naidu | 623/21.12 |
| 8,123,814 | B2 | * | 2/2012 | Meridew et al. | 623/22.28 |
| 8,123,815 | B2 | * | 2/2012 | Meridew et al. | 623/22.29 |
| 8,398,718 | B2 | * | 3/2013 | Richardson et al. | 623/22.17 |
| 8,920,510 | B2 | * | 12/2014 | Forsell | A61F 2/32 |
| | | | | | 623/22.15 |
| 9,168,066 | B2 | * | 10/2015 | Regala | A61B 17/68 |
| 2001/0008981 | A1 | * | 7/2001 | Masini | 623/22.42 |
| 2002/0128720 | A1 | * | 9/2002 | Masini | 623/22.42 |
| 2003/0055510 | A1 | * | 3/2003 | Bunz | 623/22.14 |
| 2003/0171817 | A1 | * | 9/2003 | Rambert et al. | 623/22.17 |
| 2004/0083004 | A1 | * | 4/2004 | Wasielewski | 623/22.24 |
| 2004/0102853 | A1 | * | 5/2004 | Boumann | A61F 2/4241 |
| | | | | | 623/21.16 |
| 2005/0004677 | A1 | * | 1/2005 | Johnson | 623/22.19 |
| 2005/0060040 | A1 | * | 3/2005 | Auxepaules | A61F 2/32 |
| | | | | | 623/22.18 |
| 2005/0159821 | A1 | | 7/2005 | Thompson | |
| 2005/0256585 | A1 | * | 11/2005 | Park | A61F 2/3603 |
| | | | | | 623/23.14 |
| 2005/0267590 | A1 | | 12/2005 | Lee | |
| 2006/0217815 | A1 | * | 9/2006 | Gibbs et al. | 623/22.17 |
| 2007/0032878 | A1 | * | 2/2007 | Bader et al. | 623/22.17 |
| 2008/0133023 | A1 | * | 6/2008 | Schlotterback et al. | 623/22.42 |
| 2008/0228283 | A1 | * | 9/2008 | Willi et al. | 623/23.35 |
| 2009/0157192 | A1 | * | 6/2009 | Stuart | 623/22.15 |
| 2010/0249943 | A1 | * | 9/2010 | Bergin et al. | 623/22.42 |
| 2011/0035021 | A1 | * | 2/2011 | Bergin et al. | 623/22.42 |
| 2011/0093087 | A1 | * | 4/2011 | Mcmahon et al. | 623/22.42 |

(56) References Cited

U.S. PATENT DOCUMENTS

| | | | |
|---|---|---|---|
| 2011/0257757 A1* | 10/2011 | Popoola et al. | 623/22.15 |
| 2012/0101588 A1* | 4/2012 | Forsell | 623/22.15 |
| 2012/0109330 A1* | 5/2012 | Forsell | 623/22.15 |
| 2012/0130503 A1* | 5/2012 | Forsell | A61F 2/34 623/22.15 |
| 2013/0018479 A1* | 1/2013 | Grotz | A61F 2/30756 623/22.14 |

* cited by examiner

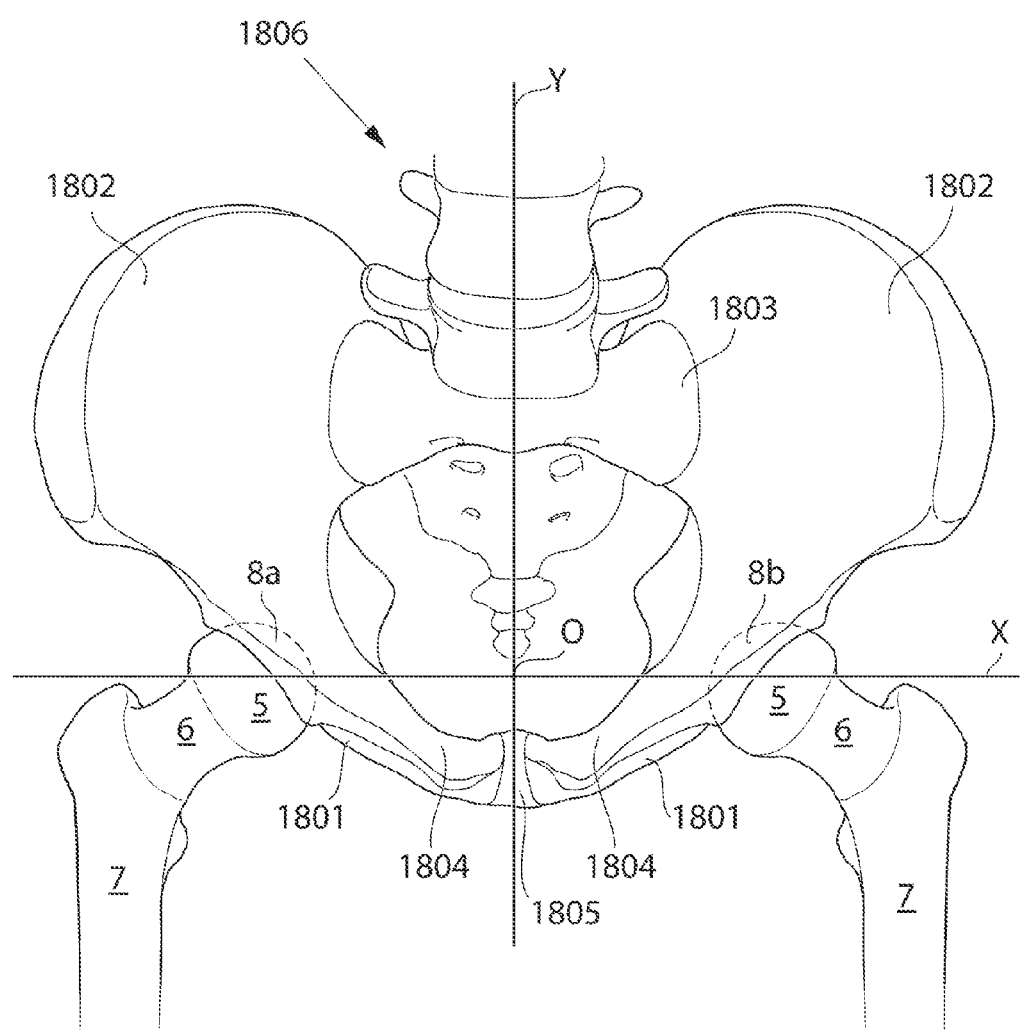

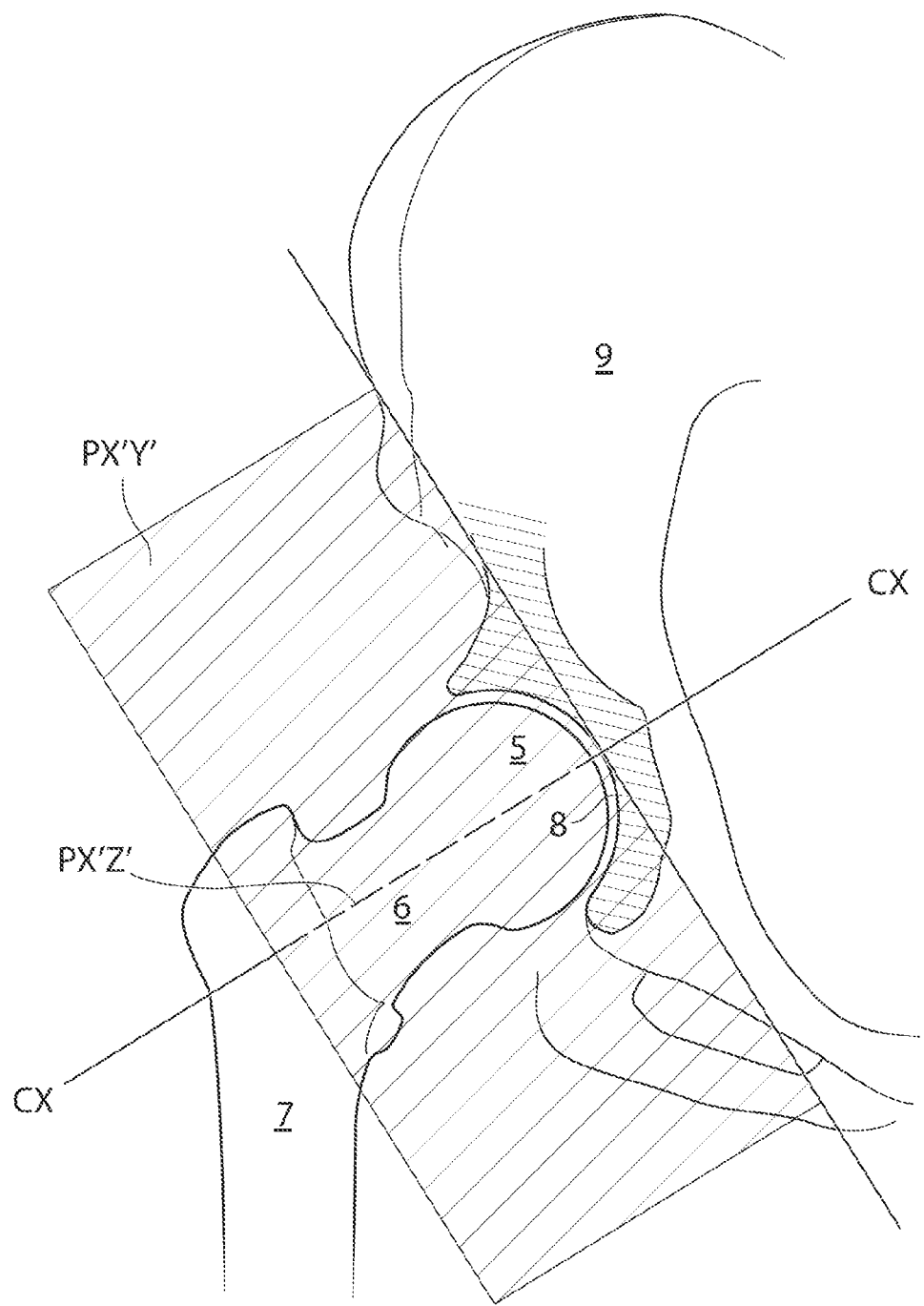

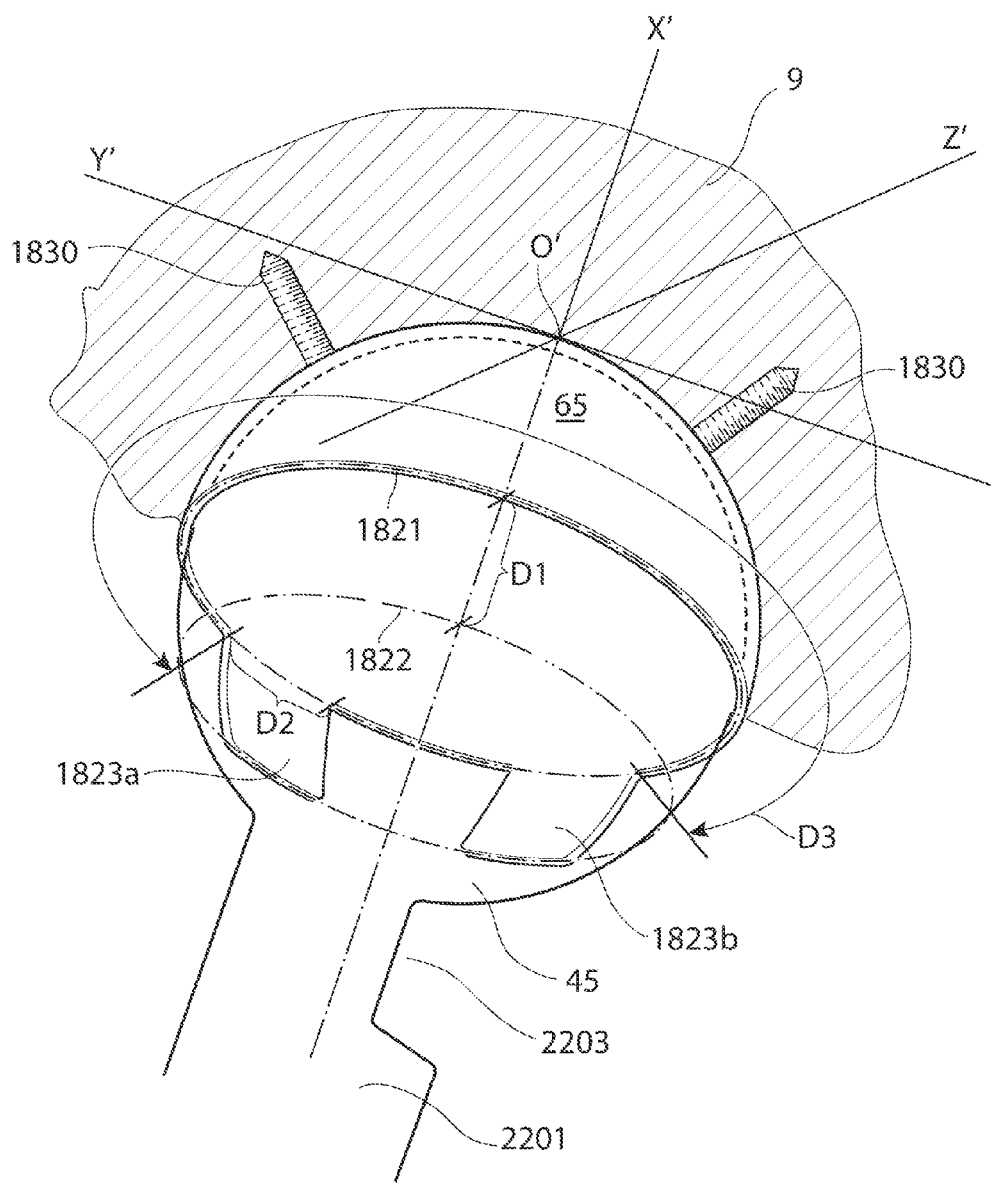

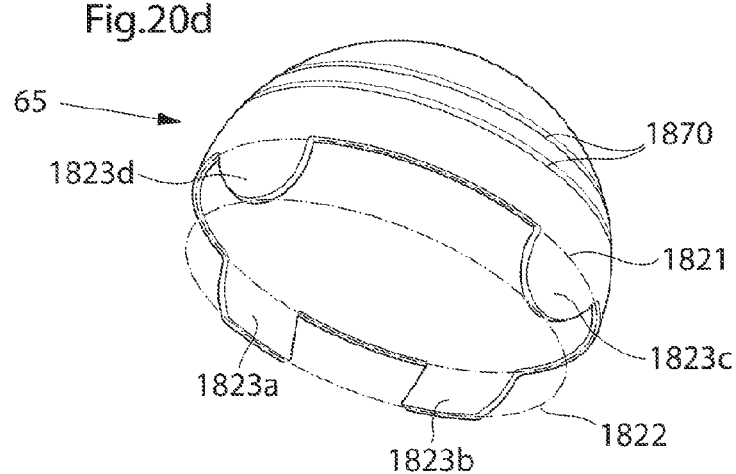
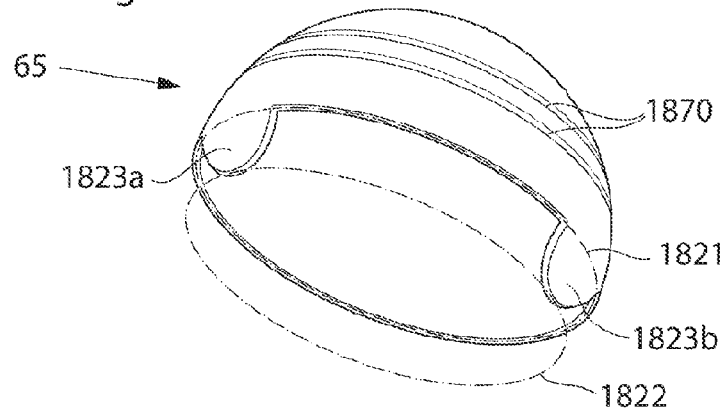
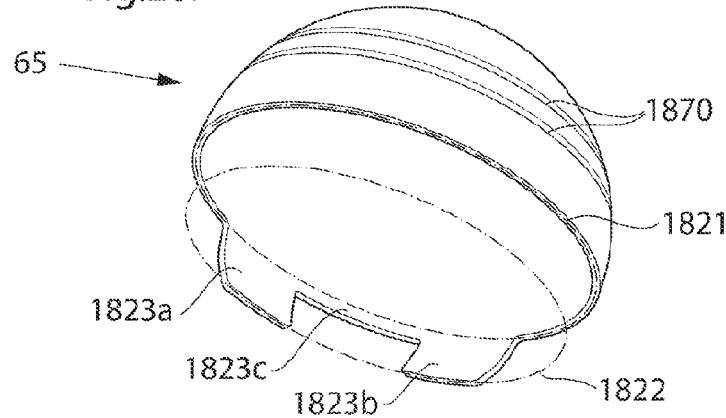

Fig.21a
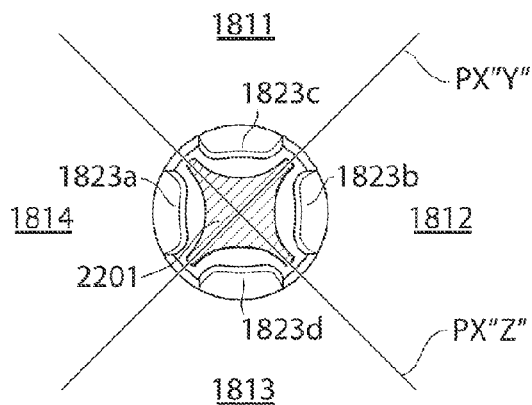
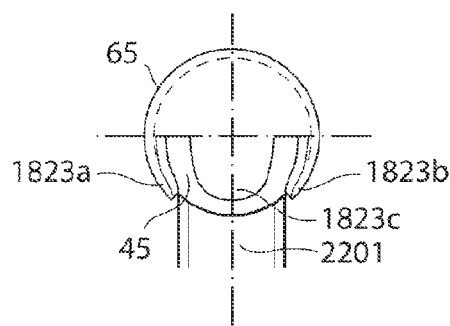
Fig.21b
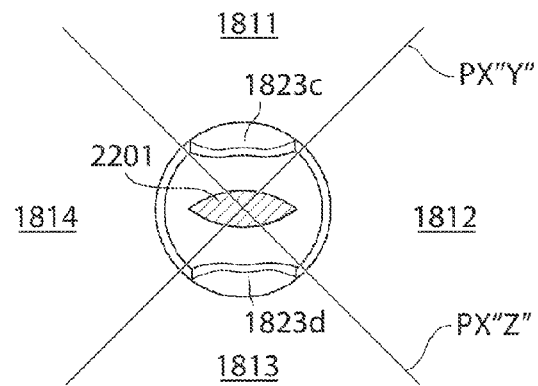
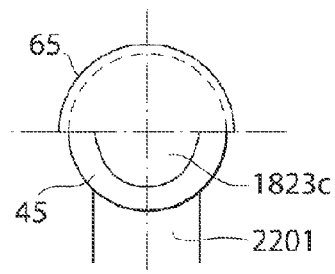

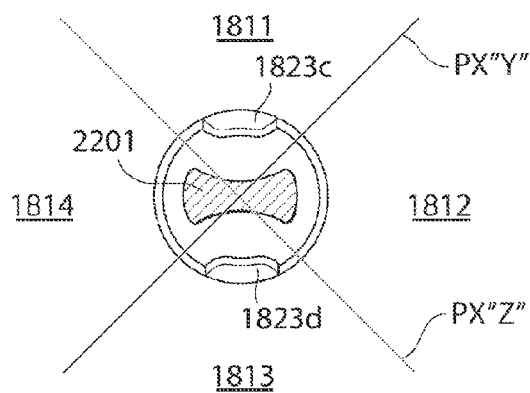
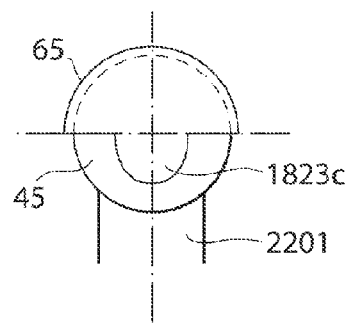
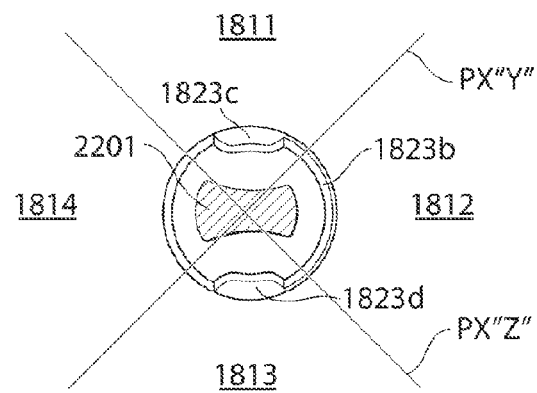
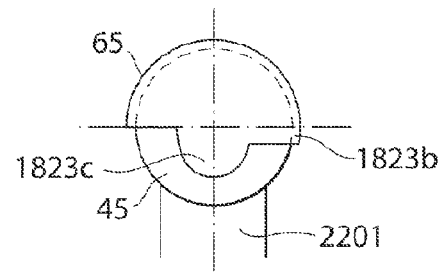

HIP JOINT DEVICE

This application is the U.S. national phase of International Application No. PCT/SE2010/050802, filed 12 Jul. 2010, which designated the U.S. and claims the benefit of U.S. Provisional No. 61/229,755, filed 30 Jul. 2009; 61/229,738 filed 30 Jul. 2009; 61/229,739 filed 30 Jul. 2009; 61/229,743 filed 30 Jul. 2009; 61/229,745 filed 30 Jul. 2009; 61/229,746 filed 30 Jul. 2009; 61/229,747 filed 30 Jul. 2009; 61/229,748 filed 30 Jul. 2009; 61/229,751 filed 30 Jul. 2009; 61/229,752 filed 30 Jul. 2009; 61/229,761 filed 30 Jul. 2009; 61/229,767 filed 30 Jul. 2009; 61/229,778 filed 30 Jul. 2009; 61/229,786 filed 30 Jul. 2009; 61/229,789 filed 30 Jul. 2009; 61/229,796 filed 30 Jul. 2009; 61/229,735 filed 30 Jul. 2009; and which claims priority to Swedish Application Nos.: 0900981-2 filed 10 Jul. 2009; 0900957-2 filed 10 Jul. 2009; 0900958-0 filed 10 Jul. 2009; 0900959-8 filed 10 Jul. 2009; 0900960-6 filed 10 Jul. 2009; 0900962-2 filed 10 Jul. 2009; 0900963-0 filed 10 Jul. 2009; 0900965-5 filed 10 Jul. 2009; 0900966-3 filed 10 Jul. 2009; 0900968-9 filed 10 Jul. 2009; 0900969-7 filed 10 Jul. 2009; 0900970-5 filed 10 Jul. 2009; 0900972-1 filed 10 Jul. 2009; 0900973-9 filed 10 Jul. 2009; 0900974-7 filed 10 Jul. 2009; 0900976-2 filed 10 Jul. 2009 and 0900978-8 filed 10 Jul. 2009, the entire contents of each of which are hereby incorporated by reference.

TECHNICAL FIELD

The present invention relates generally to medical devices for implantation in a hip joint.

BACKGROUND ART

The hip joint is a synovial joint, joining the pelvis to the proximal portion of the femoral bone. Synovial joint are the most common types of joints in mammals, and are typical of nearly all limb joints. The contacting surfaces of said the pelvic, the acetabulum, and the contacting surface of the femoral bone, the caput femur, are smooth and rounded, and covered by articular cartilage. A synovial membrane, encapsulates the joint, forming a hip joint cavity, which contains synovial fluid. Outside the synovial membrane is a fibrous capsule and ligaments, forming an articular capsule.

There are both natural and pathological processes leading to deteriorated joint function. With age and wear, the articular cartilage becomes less effective as a shock absorber and a lubricated surface. Different degenerative joint diseases, such as arthritis, osteoartrithis, or osteoarthrosis, accelerate the deterioration.

Hip joint Osteoarthritis is a syndrome in which low-grade inflammation results in pain in the hip joints, caused by abnormal wearing of the Cartilage that acts as a cushion inside if the hip joint. This abnormal wearing of the cartilage also results in a decrease of the joints lubricating fluid called Synovial fluid. Hip joint Osteoarthritis is estimated to affect 80% of all people over 65 years of age, in more or less serious forms.

The present treatment for hip osteoarthritis comprises NSAID drugs, local injections of Hyaluronic acid or Glucocorticoid to help lubricating the hip joint, and replacing part of the hip joint with a prosthesis through hip joint surgery.

The replacing of parts of the hip joint is one of the most common surgeries to date performed at hundreds of thousands of patients in the world every year. The most common method comprises placing a metal prosthesis in Femur and a plastic bowl in Acetabulum. This operation is done through an incision in the hip and upper thigh and through Fascia Lata and the lateral muscles of the thigh. To get access to the joint, the supporting Capsule attached to Femur and Ilium needs to be penetrated, making it difficult to get a fully functional joint after the surgery. Femur is then cut at the neck with a bone saw and the prosthesis is placed in femur either with bone cement or without. Acetabulum is slightly enlarged using an Acetabular reamer, and the plastic bowl is positioned using screws or bone cement.

The complications after hip joint surgery includes dislocation of the hip joint and loosening of the prosthesis from its fixation in the femoral bone. The loosening and/or dislocation of the prosthesis could be induced by an abnormal strain being placed on the hip joint from e.g. the patient falling or making a rapid movement of the hip, or by a bodily macrophage reaction.

SUMMARY

A medical device for implantation in a hip joint of a patient is provided. The hip joint having a caput femur integrated with a collum femur having a collum and caput center axis, extending longitudinal along the collum and caput femur, in the center thereof. The medical device comprises: an elongated portion adapted to at least partially replace the collum femur, wherein said elongated portion is adapted to be connected to a prosthetic spherical portion adapted to replace the caput femur, and wherein said prosthetic spherical portion in turn is adapted to be movably placed in a prosthetic replacement for the acetabulum comprising at least one extending portion adapted to clasp said prosthetic spherical portion. The elongated portion comprises a restricting portion adapted to restrict the motion range of the spherical portion in relation to the prosthetic replacement for the acetabulum. The restricting portion of the elongated portion is adapted to enable an advantageous motion range in relation to the prosthetic replacement for the acetabulum.

According to one embodiment, the elongated portion comprises at least one recess adapted to receive a portion of said prosthetic artificial acetabulum, when implanted. The recess could be adapted to be placed frontal to the coronal pelvis plane, when implanted and being in the defined base position, (further defined with reference to FIG. 1b).

The recess could adapted to be placed in the frontal quadrant or adapted to be placed in the dorsal quadrant or adapted to be placed in the proximal quadrant or adapted to be placed in the distal quadrant or adapted to be placed in the frontal quadrant, when implanted and being in the base position.

According to one embodiment, the recess is more than 2 mm deep, according to another embodiment, the recess is more than 4 mm deep, according to another embodiment, the recess is more than 6 mm deep, according to another embodiment, the recess is more than 8 mm deep.

The elongated portion could according to one embodiment comprise an adaptation adapted to receive said extending portion when implanted. The adaptation could comprise a bent portion of the elongated portion.

The bent portion could be bent such that the restricting portion of the elongated portion mainly is placed frontal to the coronal pelvis plane, when implanted and being in the base position.

The bent portion could be bent such that the restricting portion of the elongated portion mainly is placed dorsal to the coronal pelvis plane, when implanted and being in the base position.

The bent portion, could according to another embodiment be bent such that the restricting portion of the elongated portion mainly is placed in the frontal quadrant, when implanted and being in the base position.

The bent portion could further be bent such that the restricting portion of the elongated portion mainly is placed in the dorsal quadrant, when implanted and being in the base position.

According to another embodiment, the bent portion is bent such that the restricting portion of the elongated portion mainly is placed in the proximal quadrant, when implanted and being in the base position.

The bent portion is bent such that said restricting portion of said elongated portion mainly is placed in the distal quadrant, when implanted and being in the base position.

According to one embodiment, a cross-section of said restricting portion of said elongated portion, perpendicular to the caput and collum center axis, comprises a first distance and a second distance, wherein a center point of a line of said first distance intersects a center point of a line of said second distance, and wherein said first distance is shorter than said second distance.

According to yet another embodiment, the first distance is a cross-sectional distance of a narrow portion if the elongated portion, and the second distance is a cross-sectional distance of a wide portion of said elongated member.

According to yet another embodiment, the restricting portion of the elongated portion is adapted to be substantially aligned with the collum center axis and adapted to be eccentrically placed in relation to the collum axis, when implanted and being in the base position.

According to another embodiment, a major portion of said restricting portion of said elongated portion is adapted to be placed frontal to the coronal pelvis plane when implanted and being in the base position.

According to another embodiment, the restricting portion of the elongated portion is adapted to be placed in the frontal quadrant, when implanted and being in the base position.

According to another embodiment, the restricting portion of the elongated portion is adapted to be placed in the dorsal quadrant, when implanted and being in the base position.

According to another embodiment, the restricting portion of the elongated portion is adapted to be placed in the proximal quadrant, when implanted and being in the base position.

According to another embodiment, the restricting portion of the elongated portion is adapted to be placed in the distal quadrant, when implanted and being in the base position.

A cross section of the restricting portion of the elongated portion, perpendicular to the collum center axis, could be circular, polygonal or elliptic.

According to one embodiment, the restricting portion, when implanted, is adapted to be placed such that adduction is restricted more degrees than flexion.

According to another embodiment, the restricting portion, when implanted, is adapted to be placed such that abduction is restricted more degrees than flexion.

According to another embodiment, the restricting portion, when implanted, is adapted to be placed such that adduction is restricted more degrees than extension.

According to another embodiment, the restricting portion, when implanted, is adapted to be placed such that abduction is restricted more degrees than extension.

A prosthetic replacement for the acetabulum comprising at least one extending portion could in any of the embodiments be adapted to clasp the spherical portion.

The prosthetic replacement for the acetabulum could comprise an inner and an outer surface. A contacting portion of said inner surface is spherical and adapted to face the center of the hip joint when said medical device is implanted. The prosthetic replacement for the acetabulum could be adapted to receive the spherical portion. The prosthetic replacement for the acetabulum could comprise at least one extending portion, extending the contacting portion of the inner surface such that the at least one extending portion clasps the spherical portion, such that the spherical portion is restrained in the medical device. The prosthetic replacement for the acetabulum could be adapted to be fixated to the pelvic bone of the patient.

The prosthetic replacement for the acetabulum could in one embodiment be adapted to receive the spherical portion being in connection with said medical device. The said inner surface comprises an equator line, being the largest circular circumference of said inner contacting surface, being a surface adapted to be in contact with said spherical portion, and the at least one extending portion passes beyond said equator line, such that the end portion of said contacting portion of said inner surface forms a circular extension line having a smaller circumference than said equator line, and the at least one extending portion circumferentially extends discontinuously along said equator line, such that a portion of said medical device can be placed between said extension line and said equator line.

According to another embodiment, the extension line is placed distal to the equator line, when the medical device is implanted.

According to another embodiment, the at least one extending portion extends circumferentially along the equator line, dorsal to the right-left axis of pelvis.

According to another embodiment, the at least one extending portion extends circumferentially along the equator line, dorsal to the coronal pelvis plane PXY and proximal to the horizontal pelvis PXZ plane.

In yet another embodiment, the at least one extending portion extends circumferentially along said equator line, dorsal to the coronal pelvis plane PXY and distal to the horizontal pelvis in a plane.

In yet another embodiment, the at least one first extending portion extends circumferentially along said equator line dorsal to the coronal pelvis plane PXY and proximal to the horizontal pelvis PXZ plane, and at least one second extending portion extends dorsal to the coronal pelvis plane PXY and distal to the horizontal pelvis PXZ plane.

The at least one extending portion could extend circumferentially along the equator line, in the proximal quadrant of the equator line.

According to another embodiment, the at least one extending portion extends circumferentially along the equator line, in the distal quadrant of the equator line.

According to another embodiment, two extending portions extends circumferentially along the equator line, in the distal and proximal quadrant thereof.

According to yet another embodiment, the at least one extending portion extends circumferentially along said equator line, in the proximal and dorsal quadrant thereof.

In yet another embodiment, the at least one extending portion extends circumferentially along said equator line, in the distal and dorsal quadrant thereof.

In yet another embodiment, the at least one extending portion extends circumferentially along said equator line, in the distal, dorsal and proximal quadrant thereof.

At least a first portion of the prosthetic replacement for the acetabulum is an extending portion, extending beyond the circular equator line, and at least a second portion is a portion not extending beyond the circular equator line. The second portion circumferentially extends along at least ¼ of said circular equator line.

The medical device could according to one embodiment have at least a first portion of the prosthetic replacement for the acetabulum being an extending portion. The extending portion extending beyond the circular equator line, and at least a second portion is a portion not extending beyond said circular equator line, wherein said second portion circumferentially extends along at least ⅓ of said circular equator line.

In yet another embodiment, at least a first portion of the prosthetic replacement for the acetabulum is an extending portion, extending beyond the circular equator line, and at least a second portion is a portion not extending beyond said circular equator line, wherein said second portion circumferentially extends along at least ½ of said circular equator line.

In yet another embodiment, at least a first portion of the prosthetic replacement for the acetabulum is an extending portion, extending beyond the circular equator line, and at least a second portion is a portion not extending beyond the circular equator line. The first portion circumferentially extends along at least ¼ of said circular equator line.

In yet another embodiment, at least a first portion of said prosthetic replacement for the acetabulum is an extending portion, extending beyond said circular equator line, and at least a second portion is a portion not extending beyond said circular equator line, wherein said first portion circumferentially extends along at least ⅓ of said circular equator line.

In yet another embodiment, at least a first portion of said prosthetic replacement for the acetabulum is an extending portion, extending beyond said circular equator line, and at least a second portion is a portion not extending beyond said circular equator line, wherein said first portion circumferentially extends along at least ½ of said circular equator line.

The medical device could according to yet another embodiment have a first extending portion, extending beyond said circular equator line, and at least a second portion is a portion not extending beyond said circular equator line, wherein said first portion circumferentially extends along at least ¹/₁₀ of said circular equator line.

In yet another embodiment, being compatible with any of the above-mentioned embodiments, at least a first portion of said prosthetic replacement for the acetabulum is an extending portion, extending beyond said circular equator line, and at least a second portion is a portion not extending beyond said circular equator line, wherein said first portion circumferentially extends along at least ¹/₁₀ of said circular equator line, and said second portion circumferentially extends along at least ¼ of said circular equator line.

In other embodiments, at least two first portions of said prosthetic replacement for the acetabulum are extending portions, extending beyond said circular equator line, and at least a second portion is a portion not extending beyond said circular equator line, wherein said first portions each circumferentially extends along at least ¹/₁₀ of said circular equator line, and said second portion circumferentially extends along at least ¼ of said circular equator line.

In further embodiment, at least two first portions of the medical device are extending portions, extending beyond said circular equator line, and wherein one of said extending portions extends further than the other extending portion.

In further embodiments the medical device further comprises two second portions not extending beyond said circular equator line, and wherein said two first extending portion circumferentially extends along said equator line between said two second portions.

In further embodiments, the extending portion is adapted to clasp the spherical portion, and the restricting portion of the elongated portion of the medical device is adapted to, when implanted in the base position, be placed such that their placement in relation to each other creates an advantageous motion range.

In further embodiments, the extending portion of the restricting portion of the elongated portion is adapted to be placed in relation to each other when implanted in the base position, such that adduction is restricted more degrees than flexion.

In yet further embodiments, the extending portion the restricting portion of the elongated portion is adapted to be placed in relation to each other when implanted in the base position, such that abduction is restricted more degrees than flexion.

In further embodiments, the extending portion of the restricting portion of the elongated portion is adapted to be placed in relation to each other when implanted in said base position, such that adduction is restricted more degrees than extension.

The extending portion of the restricting portion of the elongated portion could further be adapted to be placed in relation to each other when implanted in the base position, such that abduction is restricted more degrees than extension.

A method for implantation in a hip joint of a patient a medical device is further provided, the hip joint having a caput femur integrated with a collum femur having a collum and caput center axis, extending longitudinal along the collum and caput femur, in the center thereof. The medical device comprises, an elongated portion adapted to at least partially replace the collum femur, wherein said elongated portion is adapted to be at least one of, integrated in and connected to, a prosthetic spherical portion adapted to replace the caput femur, and wherein said prosthetic spherical portion in turn is adapted to be movably placed in a prosthetic replacement for the acetabulum having at least one extending portion for clasping said prosthetic spherical portion. The method comprising the steps of cutting the skin of a patient in the region of a hip joint, dissecting the hip joint, placing the medical device in the hip joint for replacing the hip joint surfaces, said extending portion comprising a restricting portion for, restricting the motion range of the spherical portion in relation to said prosthetic replacement for the acetabulum, and wherein said elongated portion comprises at least one recess, receiving in said recess a portion of said prosthetic artificial acetabulum, the restricting portion, and enabling an advantageous motion range in relation to said prosthetic replacement for the acetabulum.

Please note that any embodiment or part of embodiment, feature, method, associated system, part of system described herein or in the associated figures may be combined in any way.

BRIEF DESCRIPTION OF DRAWINGS

The invention is now described, by way of example, with reference to the accompanying drawings, in which
FIG. 1a shows pelvis in a frontal view,
FIG. 3a shows the hip joint in section.

FIG. 11 shows the hip joint in section, when a prosthetic replacement for the acetabulum, and a medical device has been implanted, FIG. 20a-20f shows embodiments of prosthetic replacements for the acetabulum, FIG. 21a-21d shows embodiments of the medical device in combination with embodiment of the prosthetic replacement for the acetabulum, in a sectional side view and in cross-section

DETAILED DESCRIPTION

Figure 1B:
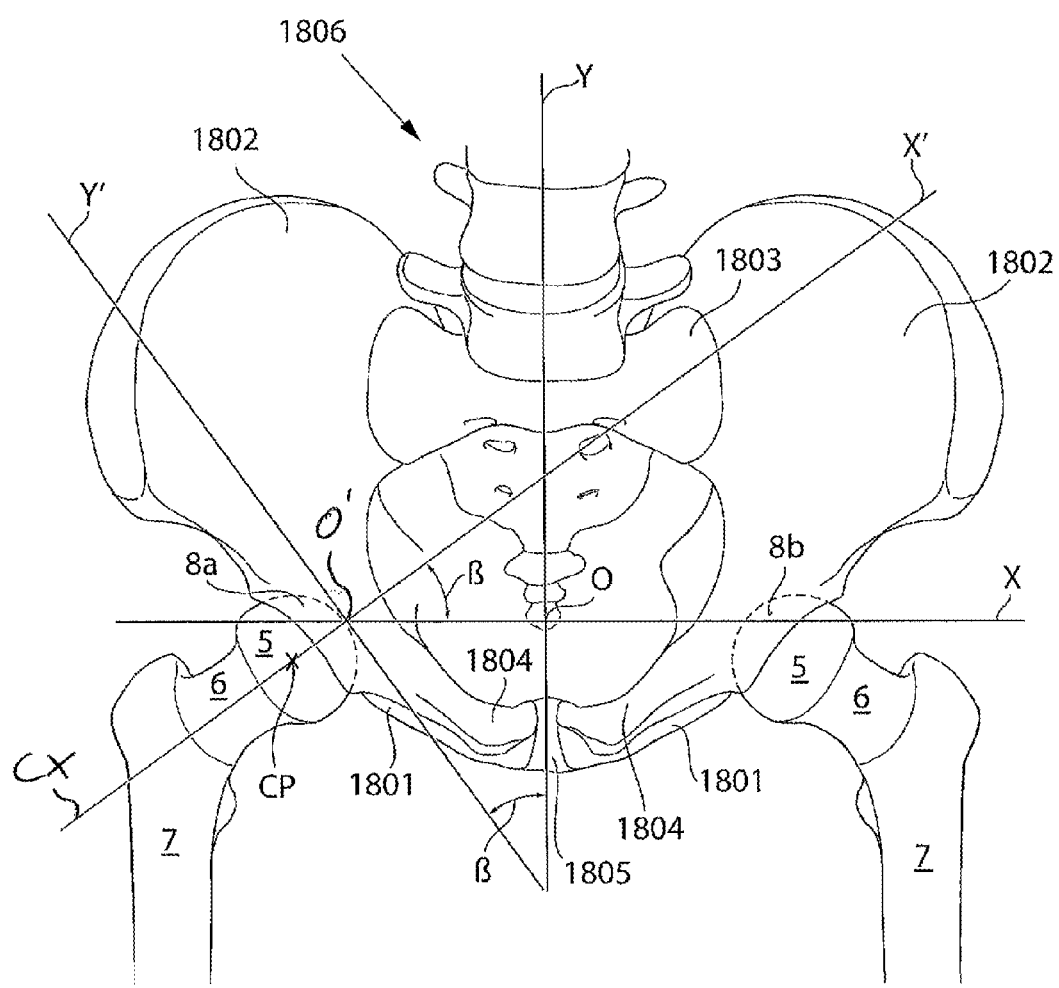
FIG. 1b shows pelvis in a frontal view.

The hip joint is a synovial ball and socket joint which permits a large motion range for allowing a plurality of different movements of the lower limb. From a neutral position the following movements of the hip joint are normally possible: Lateral or external rotation, 30° with the hip extended, 50° with the hip flexed, medial or internal rotation 40°, extension or retroversion 20°, flexion or anteversion 140°, abduction 50° with hip extended, 80° with hip flexed, adduction 30° with hip extended, 20° with hip flexed.

When replacing the natural hip joint with a prosthetic hip joint, the depth of the prosthetic acetabulum will affect the motion range, the deeper the acetabulum bowl is made the more restrictive it is to the motion range. A deeper bowl has the advantage of reducing the risk of hip joint luxation, the risk of which is a major drawback with prosthetic hips of today.

The anatomy of the hip joint and its surroundings is further disclosed in Marieb et al., Human Anatomy, 2003, Benjamin Cummings, San Francisco, pages 195-202 and in Moore et al., Clinically oriented anatomy, 1999, Lippincott; Williams & Wilkins, Baltimore, pages 501-653, both hereby incorporated by reference.

Centrally in the body should herein be understood as a point of reference located at the intersection of the Median plane and the Coronal plane and in the center part of the heart along a longitudinal axis (Caudal-Cranial). Proximal and distal are direction or location terms used in relation to said point centrally in the body and hence a distal point is a point farther away from the central point in relation a proximal point of the same structure. Any plane disclosed herein is to be understood as having infinite extension. Other anatomical terms used herein are further described in Moore et al., Clinically oriented anatomy, 1999, Lippincott, Williams & Wilkins, Baltimore, pages 2-10, which is hereby incorporated by reference.

Functional hip movements are to be understood as movements of the hip that at least partly correspond to the natural movements of the hip. On some occasions the natural movements of the hip joint might be somewhat limited or altered after hip joint surgery, which makes the functional hip movements of a hip joint with prosthetic surfaces somewhat different than the functional hip movements of a natural hip joint.

Everyday activities is to be understood as activities which are not connected to any extreme movements, such that some physical sports require. For example, everyday activities comprise: walking, sitting, cycling etc.

The functional position of an implantable medical device or prosthesis is the position in which the hip joint can perform functional hip movements. The final position is to be understood as a functional position in which the medical device needs no further position change to function.

Arthroscopy is to be understood as key hole surgery performed in a joint, since the arthroscopic procedure could be performed in the abdomen of the patient some of the steps of this arthroscopic procedure is more laparoscopic, however for the purpose of this invention the two terms arthroscopy and laparoscopy is used synonymously and for the purpose of this invention the main purpose of these methods are is that they are minimally invasive.

Elastic deformation is when a material deforms under stress (e.g. external forces), but returns to its original shape when the stress is removed. A more elastic material is to be understood as a material having a lower modulus of elasticity. The elastic modulus of an object is defined as the slope of its stress-strain curve in the elastic deformation region. The elastic modulus is calculated as stress/strain, where stress is the force causing the deformation, divided by the area to which the force is applied; and strain is the ratio of the change caused by the stress.

Elasticity is to be understood as a materials ability to deform in an elastic way.

Stiffness is to be understood as the resistance of an elastic body to deformation by an applied force.

Biocompatible material is to be understood as being a material with low level of immune response. Biocompatible materials are sometimes also referred to as biomaterials. Analogous is biocompatible metals a biocompatible metal with low immune response such as titanium or tantalum. The biocompatible metal could also be a biocompatible alloy comprising at least one biocompatible metal.

Form fitting is to be understood as an element having a part or section which is adapted to enable a mechanical connection of said element to at least one other element using said part or section. Form fitted structure is a structure of an element which enables form fitting.

In the following a detailed description of embodiments of the present invention will be given. In the drawing figures, like reference numerals designate identical or corresponding elements throughout the several figures. It will be appreciated that these figures are for illustration only and are not in any way restricting the scope of the invention Thus, any references to direction, such as "up" or "down", are only referring to the directions shown in the figures. Also, any dimensions etc. shown in the figures are for illustration purposes.

FIG. 1a shows the pelvis in a frontal view. Pelvis comprises the right and left hip bone making up the pelvic bone, in turn comprising the Sacrum 1803, Ilium 1802, Pubis 1804 and Ischium 1801. The hip joint houses the right and left acetabulum 8a,b placed laterally and distally in the pelvis. The acetabulum 8a,b being a spherically shaped cavity in the hip bones making up one of the parts of the hip joint, the acetabulum 8a,b being adapted to house the caput femur 5, being the proximal portion of the femoral bone 7 having a spherical contacting surface adapted to be placed in the acetabulum 8a,b and thus creating the operable hip joint. The pelvis has a right-left axis X extending substantially from the bottom of the left acetabulum 8a to the bottom of the right acetabulum 8b, the pelvis further having a caudal-cranial axis Y extending perpendicular to said right-left axis, centrally and substantially along the length of the patient, passing the dorsal portions of the pubic symphysis 1805 and substantially following the spinal cord 1806, intersecting the left-right axis X.

FIG. 1b shows the pelvis in a frontal view disclosing a second, displaced coordinate system. The second displaced coordinate system has its origin O' in the bottom of the acetabulum bowl 8a. The axis X and Y have, in a frontal view, been rotated the angle β, creating the axis X' and Y'. In the defined base position, the acetabulum center axis X' is aligned with the caput and collum femur center axis CX the caput and collum femur center axis CX is an axis in the extension of the collum and caput femur axis, in the center thereof. The hip joint substantially being in it base position when the patient is standing up or lying down. In said base position, the acetabulum center axis X' goes through a point O' being the origin O' in the bottom of the acetabulum bowl 8a, and a center point CP, being a point in the center of a circle defined by the edges of the acetabulum bowl 8a, and further trough the top of the caput femur 5 and following inside of the collum femur 6, aligned with the collum femur 6. The axis Y' is perpendicular to the axis X' and goes through the origin O' in the bottom of the acetabulum bowl 8a, parallel to a plane defined by the circle defined by the edges of the acetabulum bowl 8a.

Figure 1C:
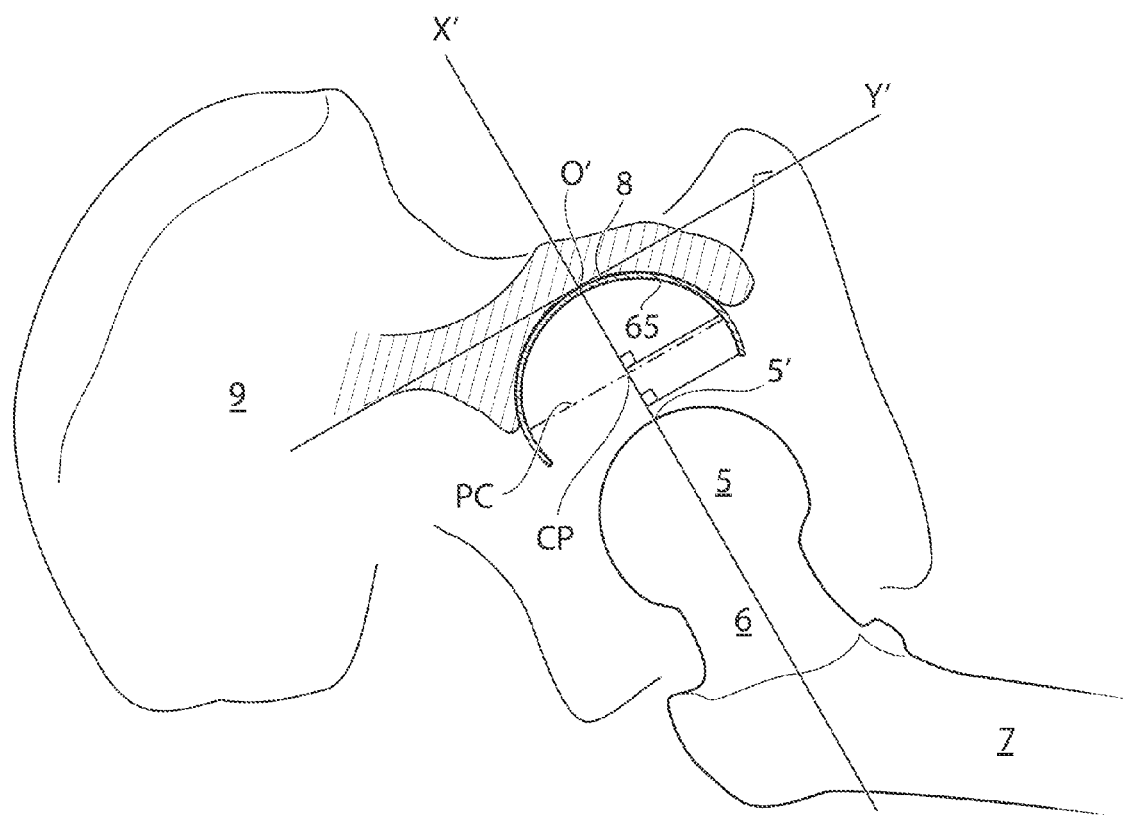
FIG. 1c shows the hip joint in section.

FIG. 1c shows the right pelvic bone 9 in section disclosing the second, displaced coordinate system. The origin O' is in the bottom of the acetabulum bowl 8. The axis X' is aligned with the caput 5 and collum 6 femur center axis CX, when the hip joint is in it base position when the patient is standing up or lying down with extended leg. In said base position the axis X' is goes through a point O' being the bottom of the acetabulum bowl 8, and a center point CP, being a point in the center of a circle defined by the edges of the acetabulum bowl 8, and further trough the top of the caput femur 5' and following inside of the collum femur 6, aligned with the collum femur 6. The axis Y' is perpendicular to the axis X', goes through the origin O' in the bottom of the acetabulum bowl 8, parallel to the plane PC defined by the circle defined by the edges of the acetabulum bowl 8.

Figure 2A:
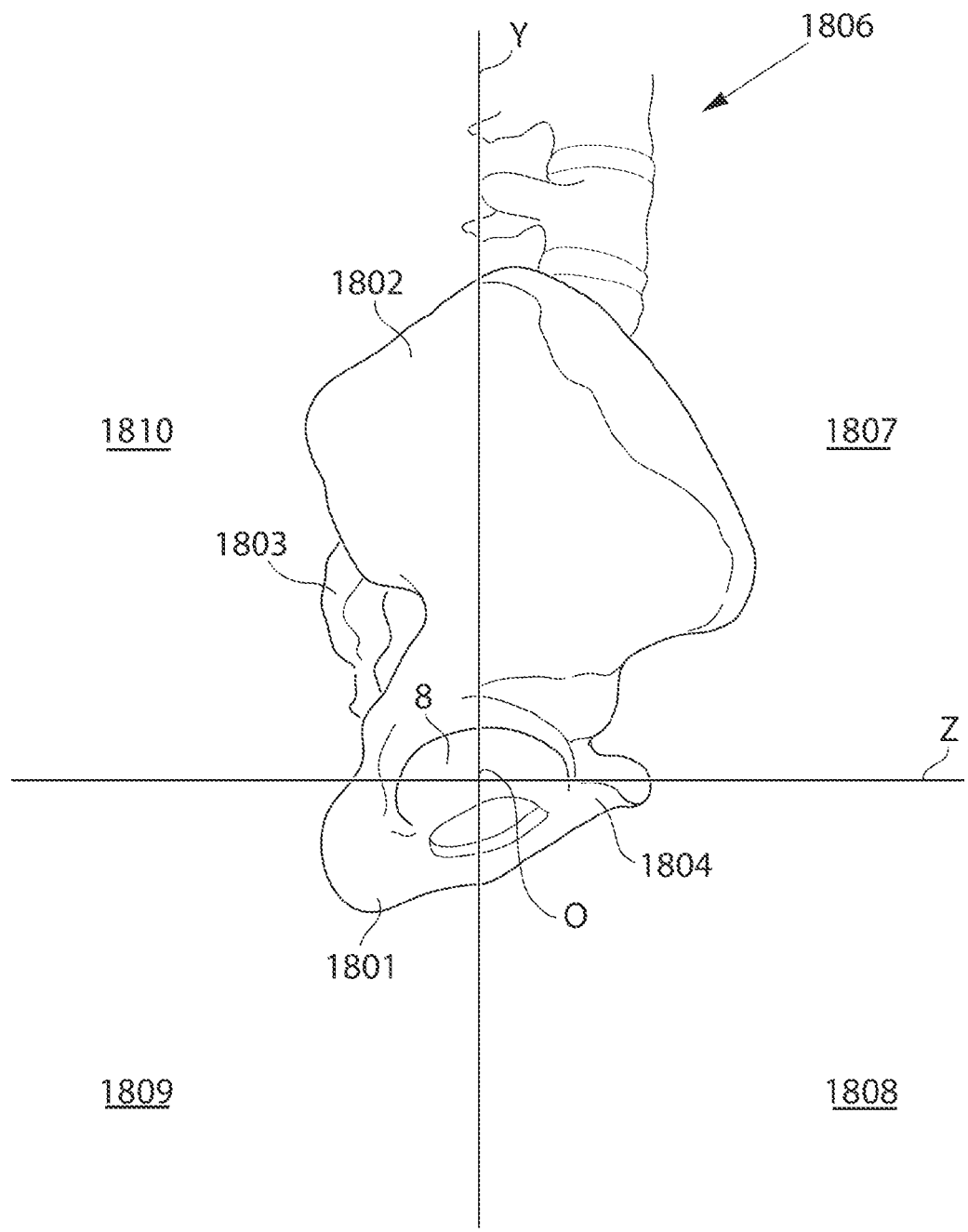
FIG. 2a shows pelvis in a lateral view.

FIG. 2a shows the pelvis in a lateral view, thus displaying the posterior side of Ilimu 1802, the anterior side of Ichum 1801, the anterior side of Pubis 1804, and Sacrum 1803 in a lateral view. The pelvis has furthermore a dorsoventral axis Z being perpendicular to the caudal-cranial axis Y and the right-left axis Y shown in FIG. 1, and intersecting them both creating a common origin O for the three axis X, Y, Z. The dorsoventral axis Z and the caudal-cranial axis Y thus being oriented such that a horizontal pelvis plane in a extends from the dorsoventral axis Z, and a coronal plane PXY extends from the dorsoventral axis Y.

Figure 2B:
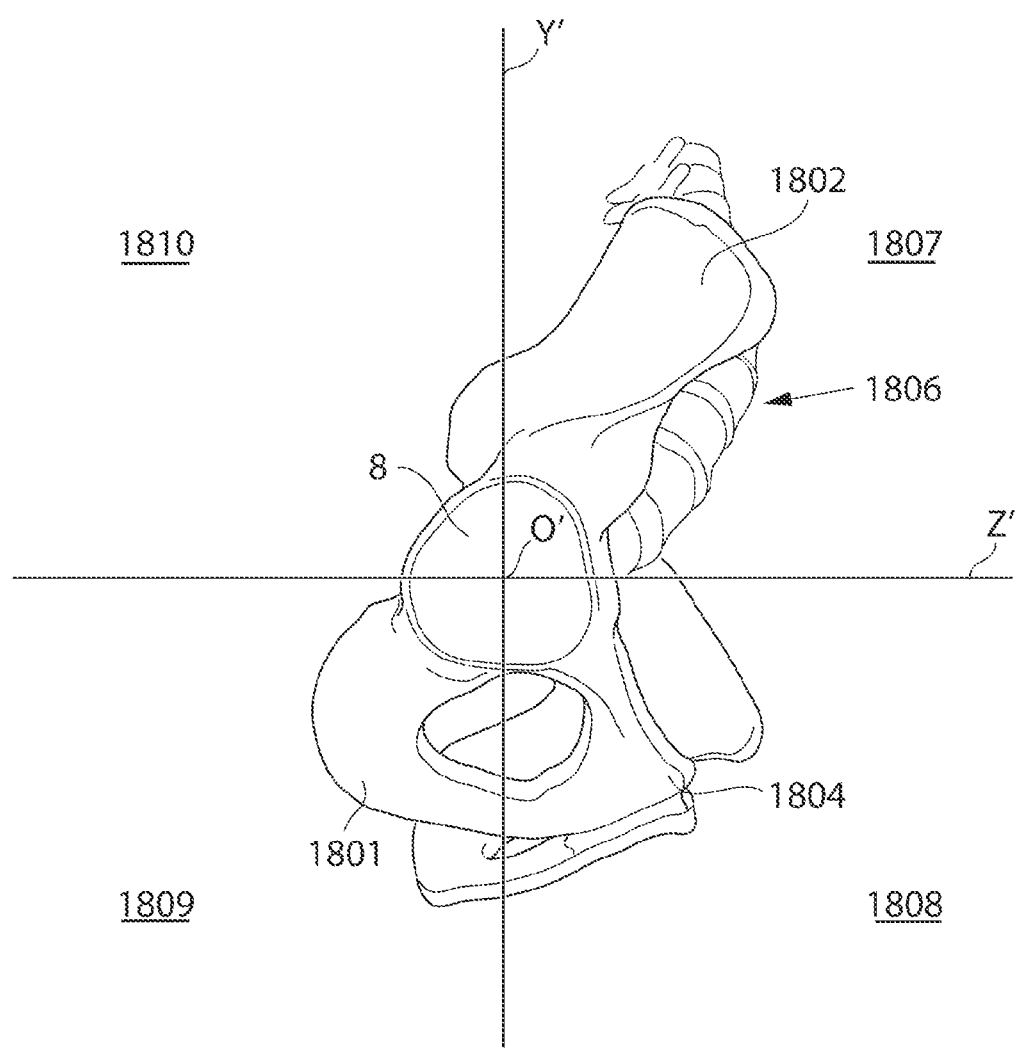
FIG. 2b shows pelvis in a lateral view.

FIG. 2b shows the pelvis in a plane view from the front and slightly from below, in the direction of the axis X' (further disclosed with reference to FIGS. 1b and 1c). The view of FIG. 2b displaying the axis Y and Z' with origin O' in the bottom of the acetabulum bowl 8 making up the acetabulum coordinate system. The axis Y', Z', in this plane view, dividing the acetabulum bowl 8 into four quadrants: the proximal-frontal quadrant 1807, the distal-frontal quadrant 1808, the distal-dorsal quadrant 1809 and the proximal-dorsal quadrant 1810.

Figure 2C:
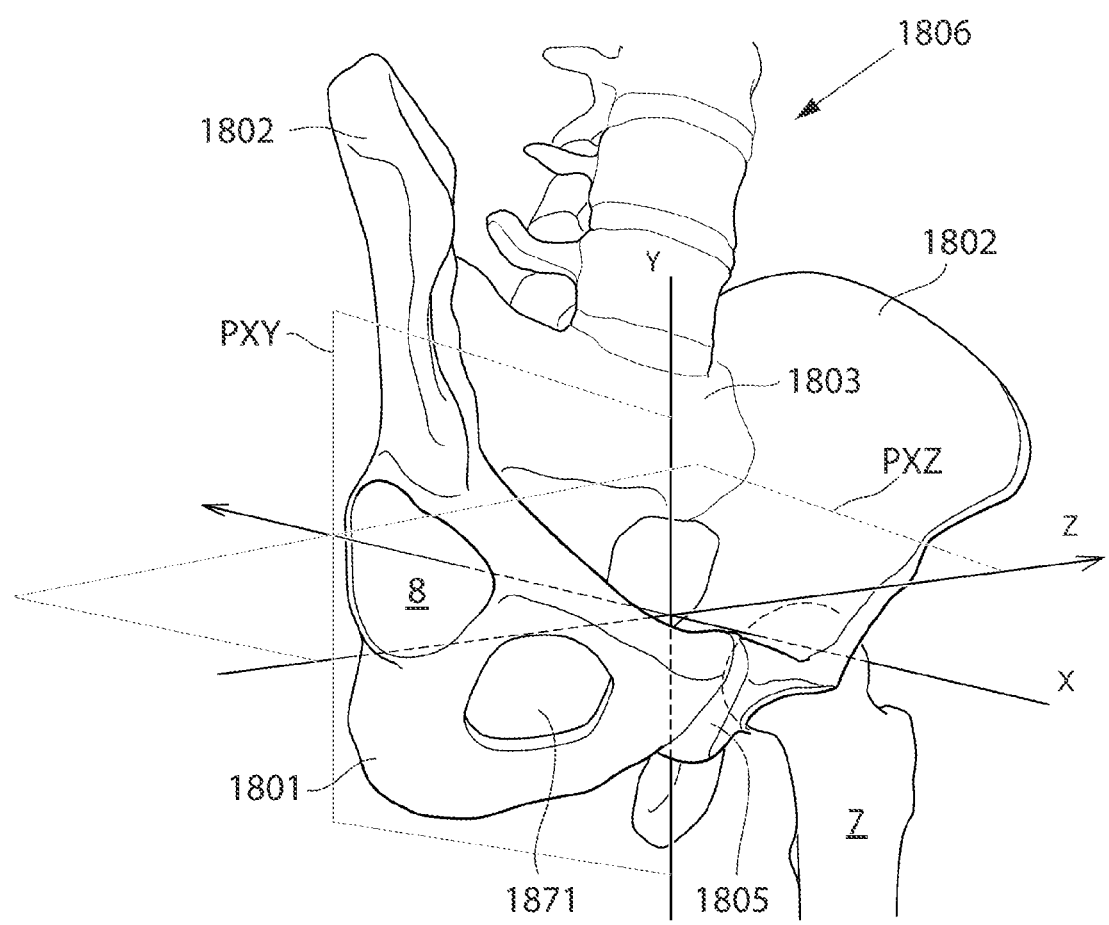
FIG. 2c shows pelvis in a perspective view from below.

FIG. 2c shows the pelvis in a perspective view from below and slightly from the front, displaying the right-left axis X passing through the center of the right and left acetabulum 8. The right-left axis X is perpendicular to the dorsoventral axis Z which also is perpendicular to the caudal-cranial axis Y. The coronal plane PXY extends from the dorsoventral axis Y, and the horizontal pelvis plane PXZ extends from the dorsoventral axis Z, thus being perpendicular to the coronal plane PXY.

Figure 2D:
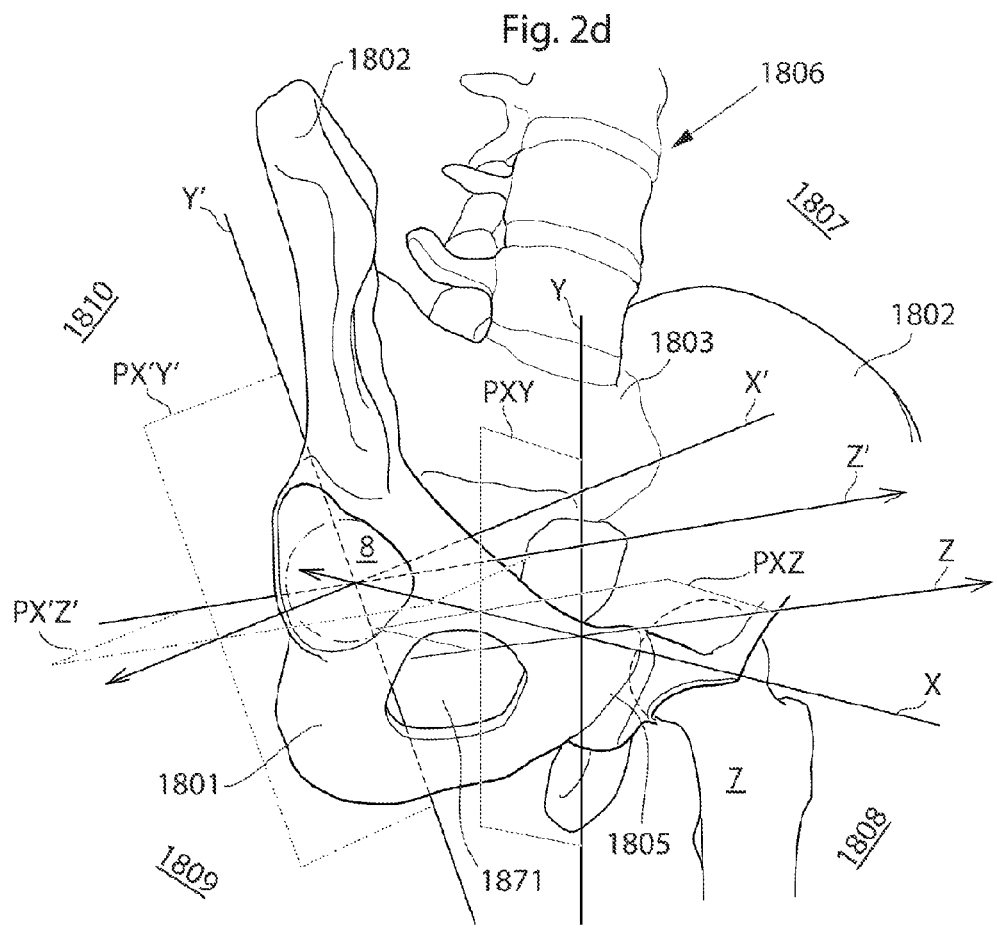
FIG. 2d shows pelvis in a perspective view from below.

FIG. 2d shows the coordinate system and planes of FIG. 2c, it further shows the second, displaced, coordinate system, being the coordinate system of the acetabulum 8, also shown in FIG. 2b. The axis of the coordinate system of acetabulum X', Y', Z' having their origin O' in the bottom of the acetabulum bowl 8, the axis X' being aligned with the caput and collum center axis. FIG. 2d further discloses the vertical acetabulum plane PXY' and the horizontal acetabulum plane PX'Y' being defined by the axis X', Y' and the vertical acetabulum plane PX'Z' being defined by the axis X', Z'. The planes PX'Y' and PX'Z' dividing the acetabulum bowl 8 into four quadrant, the proximal-frontal quadrant 1807, the distal-frontal quadrant 1808, the distal-dorsal quadrant 1809 and the proximal-dorsal quadrant 1810, in accordance with what is previously disclosed, with reference to FIG. 2b. FIG. 2d further shows the location of foramen obturatum 1871.

Figure 2E:
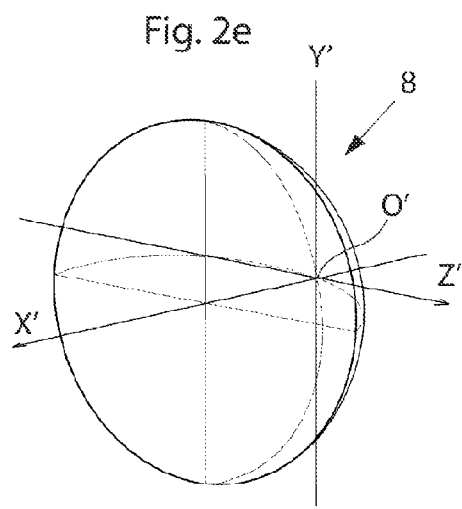
FIG. 2e shows the acetabulum, schematically.

FIG. 2e shows, schematically how the acetabulum coordinate system X', Y', Z' relates to the hemisphere defined by the acetabulum bowl 8.

Figure 2F:
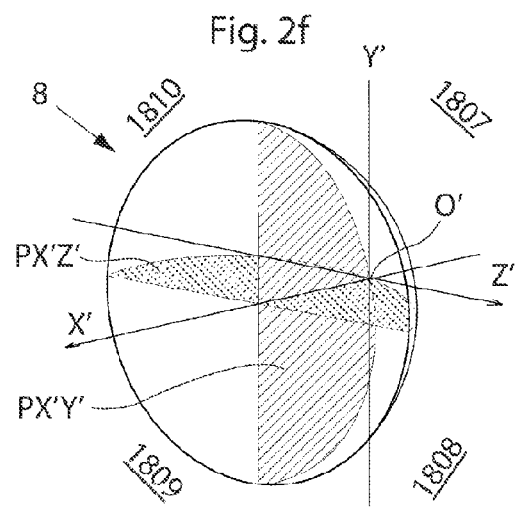
FIG. 2f shows the acetabulum, schematically.

FIG. 2f shows, schematically, how the vertical acetabulum plane PX'Y', and the horizontal acetabulum plane PX'Z' divides the acetabulum 8 into four quadrant; the proximal-frontal quadrant 1807, the distal-frontal quadrant 1808, the distal-dorsal quadrant 1809 and the proximal-dorsal quadrant 1810, in accordance with the previously disclosed, with reference to FIGS. 2b and 2d.

Figure 2G:
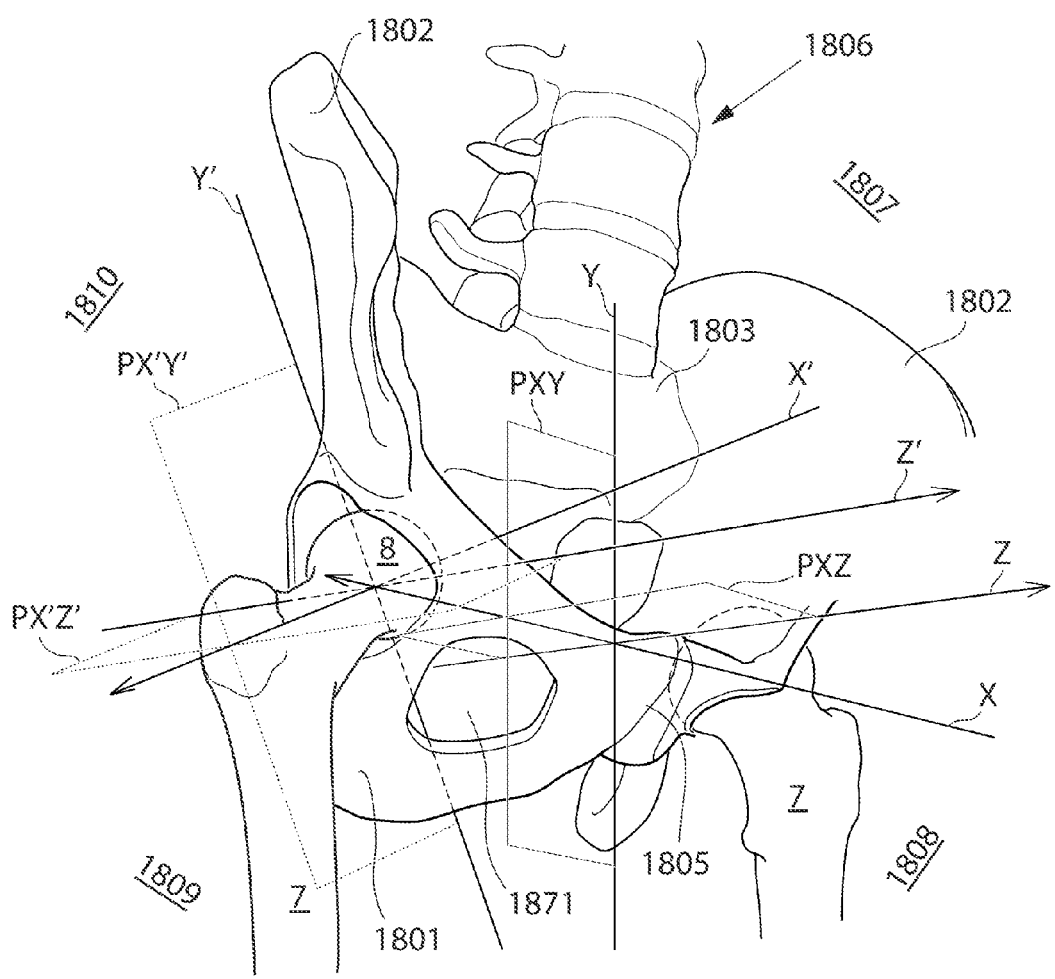
FIG. 2g shows pelvis in a perspective view from below.

FIG. 2g shows the view of FIG. 2d, and in addition it shows the horizontal and vertical acetabulum planes PX'Y' and PX'Z' also being the caput and collum femur horizontal and vertical planes PX'Y' and PX'Y', analogically dividing the caput and collum femur into four quadrants.

FIG. 3a shows a perspective view of the hip joint in section, displaying the horizontal and vertical planes PX'Y' and PX'Z' originating from the caput 5 and collum 6 center axis CX and dividing the caput 5 and collum 6 femur into quadrants.

Figure 3B:
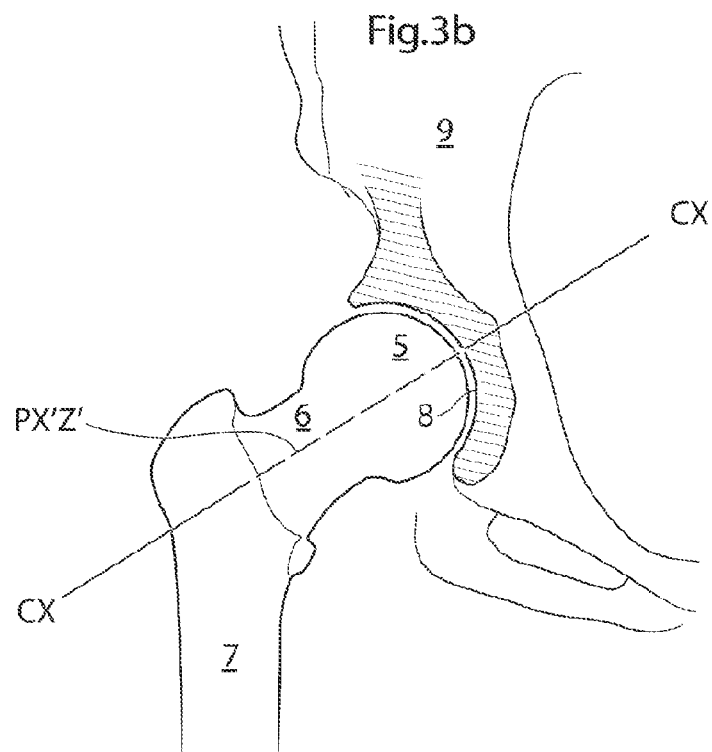
FIG. 3b shows the hip joint in section, separated.
Figure 3C:
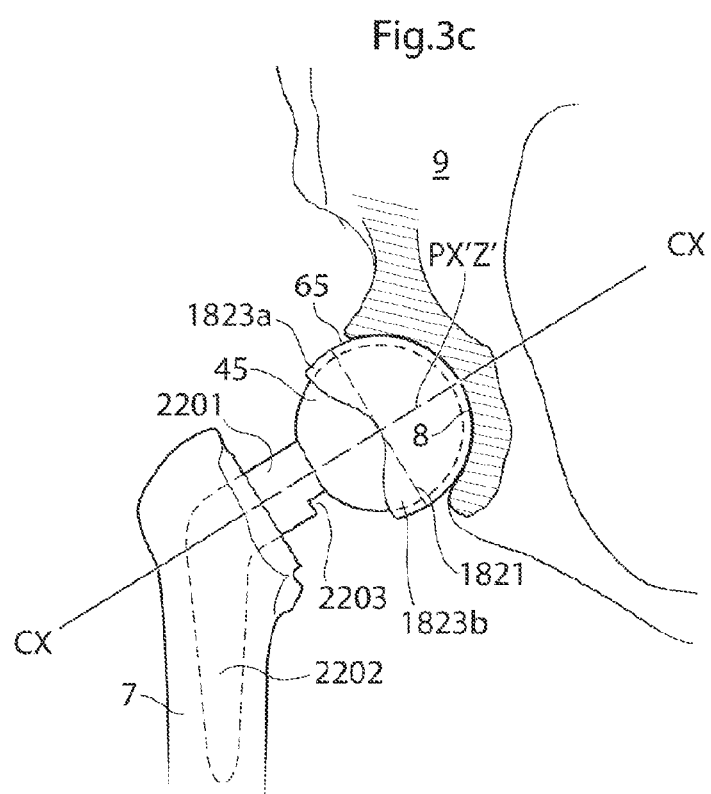
FIG. 3c shows the hip joint in section, with a prosthetic femoral stem.

FIG. 3c shows the view of FIG. 3b when a prosthetic acetabulum surface 65 has been placed in the acetabulum bowl 8 replacing the natural contacting surface of the acetabulum 8. The prosthetic replacement for the acetabulum 8 comprises two extending portions 1823a,b adapted to clasp the spherical portion 45 being a prosthetic part adapted to replace the natural collum femur 5 and thus further restraining the prosthetic spherical replacement for the caput femur 45 in the prosthetic replacement for the acetabulum 65. The prosthetic replacement for the acetabulum 65 and the prosthetic spherical replacement for the caput femur 45 combined creating a functional prosthetic hip joint FIG. 3c further shows an elongated portion 2201, adapted to at least partially replace the collum femur. The prosthetic spherical portion 45 and the elongated portion 2201 are connected to each other at the proximal portion of the elongated portion 2201. According to the embodiment shown in FIG. 3c the elongated portion 2201 is connected to a fixating portion 2202 adapted to be placed and fixated inside of the femoral bone 7. The elongated portion 2201 restrict the movement of the spherical portion 45 in relation to the prosthetic replacement for the acetabulum 65, especially since the prosthetic replacement for the acetabulum comprises extending portions 1823a,b extending beyond the equator line of the prosthetic replacement for the acetabulum. The elongated portion thus further comprises a recess 2203 for enabling further movement of spherical portion 45 connected to the elongated portion 2201 in relation to the prosthetic replacement for the acetabulum 65.

Figure 3D:
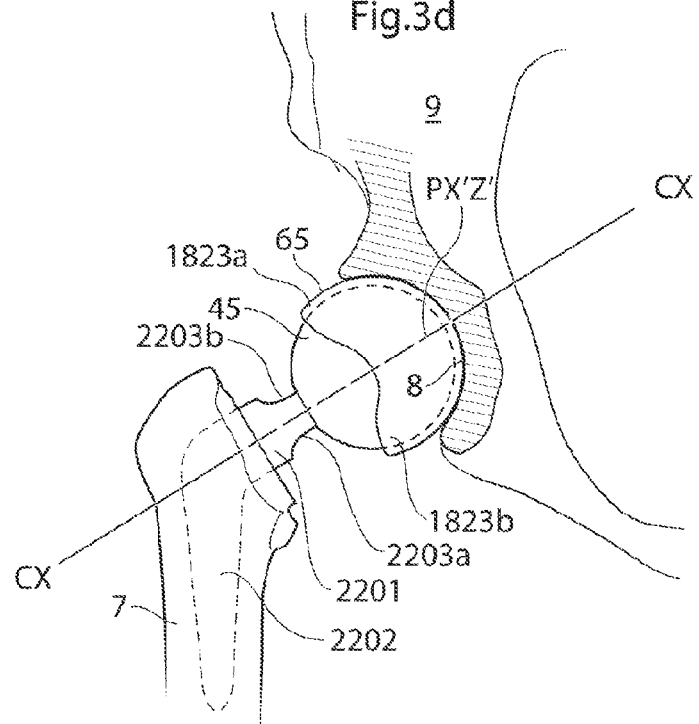
FIG. 3d shows the hip joint in section, with a prosthetic femoral stem.

FIG. 3d shows a perspective view of the hip joint in section, similar to the embodiment shown in FIG. 3c. However, in the embodiment of FIG. 3d the elongated portion 2201 comprises two recesses 2203a,b, placed such that the elongated portion 2201 are adapted to receive the extending portions 1823a,b through the extending portions 1823a,b entering the recesses 2203a,b of the elongated portion 2201 when the elongated 2201 and spherical 45 portions move in relation to the prosthetic replacement for the acetabulum 65.

Figure 3E:
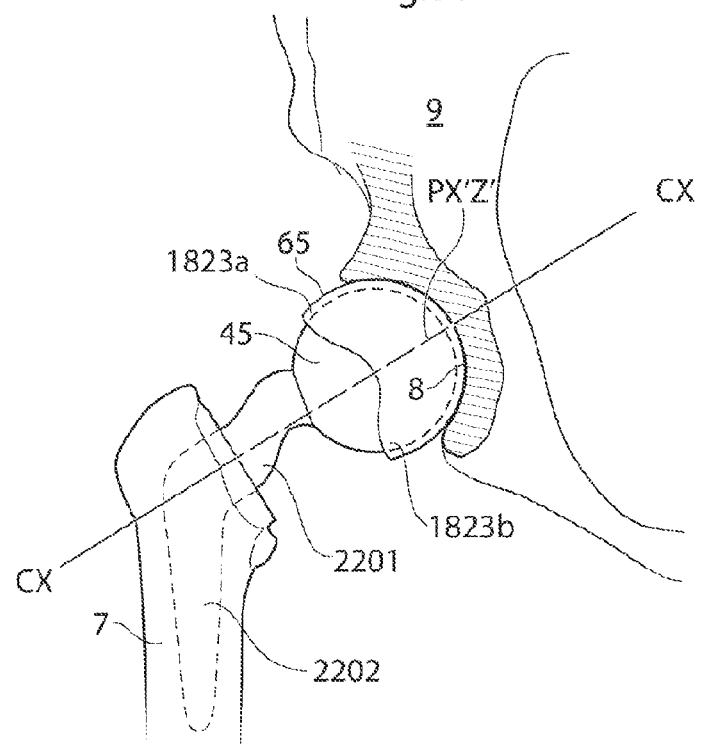
FIG. 3e shows the hip joint in section, with a prosthetic femoral stem.

FIG. 3e shows a perspective view of the hip joint in section, similar to the embodiment shown in FIGS. 3c and 3d. However, in the embodiment of FIG. 3d the elongated portion 2201 is shaped such that the contacting portion between the elongated portion 2201 and the spherical portion 45 is eccentrically placed in relation to the center axis CX of the collum and caput femur. Me eccentrically placed contacting portion enables the spherical portion with the elongated portion to move more in one direction than in another. This embodiment, similar to the recess embodiments previously disclosed, enables the adaptation of the elongated member to the prosthetic replacement for the acetabulum 65, and in particular the extending portions 1823a,b thereof, for enabling a particular motion pattern of the hip joint and thus the leg.

Figure 4A:
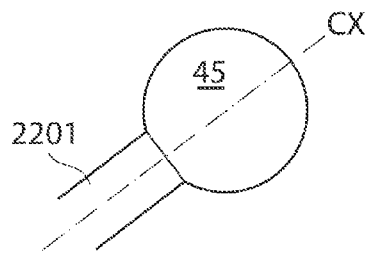
FIG. 4a-4d shows embodiments of the medical device, in side views.

FIG. 4a shows a prosthetic spherical portion 45 and a prosthetic elongated portion 2201 in a schematic view, displaying the prosthetic elongated portion 2201 being connected to the prosthetic spherical portion 45. According to the embodiment shown in FIG. 4a the elongated portion 2201 does not have any recesses or adaptations facilitating the movement of the prosthetic portions in relation to a prosthetic replacement for the acetabulum comprising extending portions.

Figure 4B:
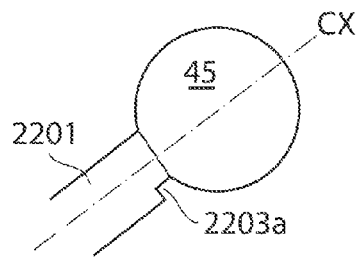

FIG. 4b shows a prosthetic spherical portion 45 and a prosthetic elongated portion 2201 in a schematic view in an embodiment where the elongated portion comprises a recess 2203a adapted to further enable movement of the prosthetic spherical 45 and elongated portions 2201 in relation to a prosthetic replacement for the acetabulum.

Figure 4C:
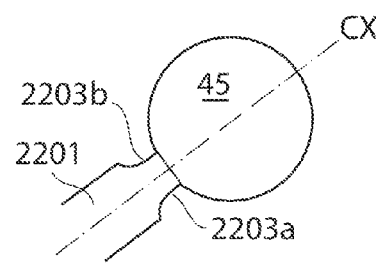

FIG. 4c shows a prosthetic spherical portion 45 and a prosthetic elongated portion 2201 in a schematic view in an embodiment in which the elongated portion 2201 comprises two recesses 2203a,b adapted to further enable movement of the prosthetic spherical 45 and elongated portions 2201 in relation to a prosthetic replacement for the acetabulum.

Figure 4D:
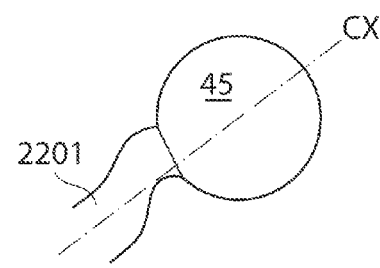

FIG. 4d shows a prosthetic spherical portion 45 and a prosthetic elongated portion 2201 in a schematic view in an embodiment in which the elongated portion 2201 is curved such that the area in which the elongated portion 2201 connects to the spherical portion 45 is eccentrically placed in relation to the collum and caput femur center axis CX.

Figure 5:
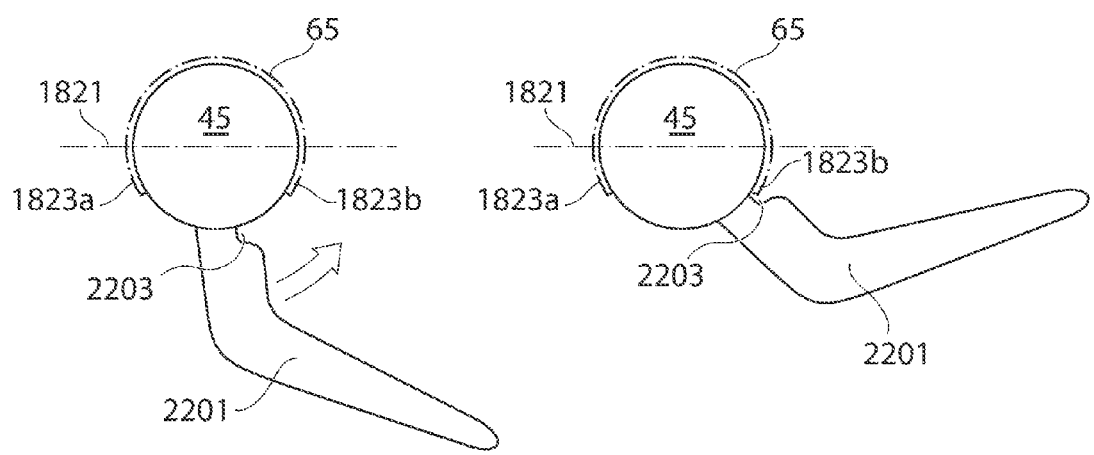
FIG. 5 shows the medical device in section, according to one embodiment.

FIG. 5 shows the prosthetic parts replacing the articulating surfaces of the hip joint. The prosthetic replacement for the acetabulum surface 65 comprises extending portions 1823a,b which are adapted to enter a recess 2203 of the prosthetic elongated portion 2201 adapted to at least partially replace the collum femur. The recess enables further movement of the prosthetic spherical 45 and elongated 2201 portion in relation to the prosthetic replacement for the acetabulum 65 in the direction of recess, such as disclosed in the right part of FIG. 5, where the prosthetic part is placed in a state in which the prosthetic spherical 45 and elongated 2201 portions are moved maximally in the direction of the recess 2203.

Figure 6A:
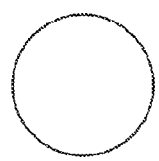
FIG. 6a-6k shows cross-sections of embodiments of the medical device.

FIG. 6a shows a cross-section of the prosthetic elongated portion without an adaptation to increase to motion range. This embodiment is disclosed in a schematic side view in FIG. 4a.

Figure 6B:
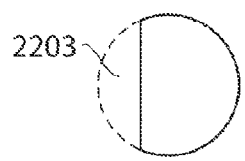

FIG. 6b shows a cross-section of the prosthetic elongated portion having a recess 2203 or adaptation such that said elongated portion is adapted for further movement in relation to a prosthetic replacement for the acetabulum in the direction of the recess 2203 or adaptation. This embodiment is disclosed in a schematic side view in FIG. 4b.

Figure 6C:
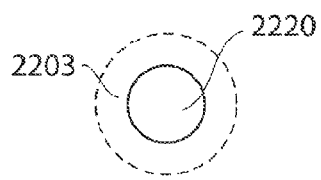

FIG. 6c shows a cross-section of the prosthetic elongated portion where the restricting part of the elongated prosthetic portion is a narrow portion 2220, with a smaller cross-sectional area than other portions of the elongated portion. In embodiments where the extending portions of a prosthetic replacement for the acetabulum extends circularly 360° around the collum and caput center axis, the circular narrow portion 2220 disclosed in FIG. 6c enables further movement of the prosthetic elongated portion in all radial directions. This embodiment is disclosed in a schematic side view in FIG. 4c.

Figure 6D:
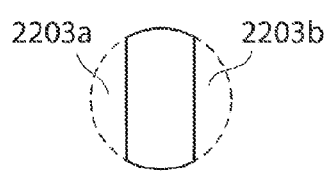

FIG. 6d shows a cross-section of the prosthetic elongated portion comprising two recesses 2203a and 2203b or adaptations, into which a prosthetic replacement for the acetabulum can enter for further increasing the motion range of the prosthetic hip joint in the directions of the recesses or adaptations. This embodiment is disclosed in a schematic side view in FIG. 4c.

Figure 6E:
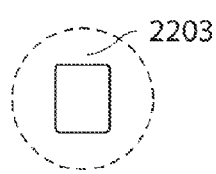

FIG. 6e shows a cross-section of the prosthetic elongated portion wherein the restricting portion of the elongated portion has a narrow square cross-section such that for increasing the motion range of the prosthetic hip joint more in the directions of the sides of the square cross-section of the restricting portion of the elongated portion. This embodiment is disclosed in a schematic side view in FIG. 4c.

Figure 6F:
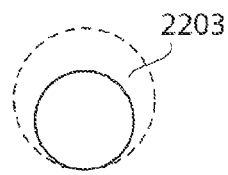

FIG. 6f shows a cross-section of the prosthetic elongated portion wherein the restricting portion of the elongated portion is more narrow that other portions of the elongated portions and eccentrically placed in relation to the caput and collum center axis. The eccentric placement of the restricting portion of the elongated portion increases the motion range of the prosthetic hip joint in the direction of the recess created by the narrow portion being placed eccentrically. This embodiment is disclosed in a schematic side view in FIG. 4b.

Figure 6G:

FIG. 6g shows a cross-section of the prosthetic elongated portion similar to the embodiment shown in FIG. 6f. However in the embodiment shown in FIG. 6g the narrow portion of the elongated portion is placed further eccentrically, further increasing the motion range of the prosthetic hip joint in the direction of the recess created by the narrow portion being placed eccentrically.

Figure 6H:
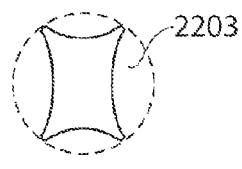

FIG. 6h shows a cross-section of the prosthetic elongated portion in which a portion of the elongated portion comprises a plurality of recesses 2203 which are adapted to a particular prosthetic replacement for the acetabulum. According to the embodiment shown in FIG. 6h the restricting portion is adapted for a prosthetic replacement for the acetabulum comprising extending portions with a circular surface entering the recess of the elongated prosthetic portion.

Figure 6I:
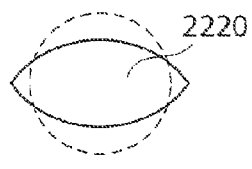

FIG. 6i shows a cross-section of the prosthetic elongated portion, wherein said cross section is a more narrow elliptically shaped cross section 2220 which enables further movement of the prosthetic elongated portion in the narrow direction of the elliptically shaped elongated portion.

Figure 6J:
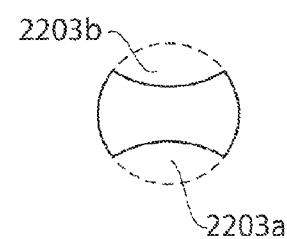

FIG. 6j shows a cross-section of the prosthetic elongated portion in which a portion of the elongated portion comprises two recesses 2203a,b which are adapted to a particular prosthetic replacement for the acetabulum. According to the embodiment shown in FIG. 6h the restricting portion is adapted for a prosthetic replacement for the acetabulum comprising extending portions with a circular surface entering the recess of the elongated prosthetic portion.

Figure 6K:
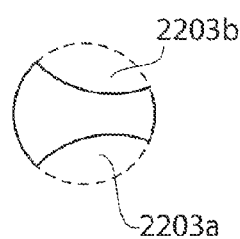

FIG. 6k shows a cross-section of the prosthetic elongated portion in an embodiment similar to the embodiment shown in FIG. 6j, however, in the embodiment of FIG. 6k the recesses 2203a,b are somewhat eccentrically placed in relation to the caput and collum center axis. The eccentrically placed recesses 2203a,b thus altering the directions in which the motion range are further increased, such that the recesses could be adapted to more critical motions that a patient is interesting in doing.

Figure 7A:
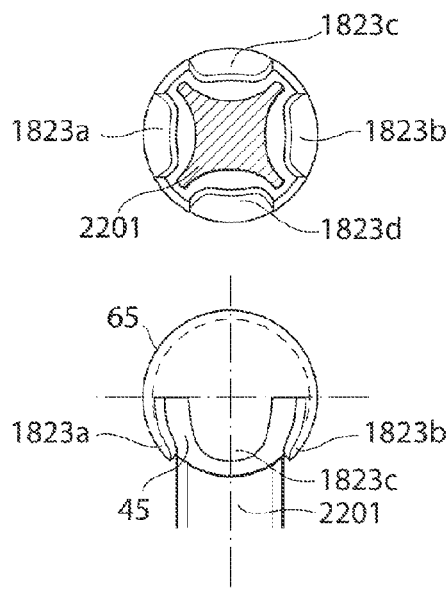
FIG. 7a-7d shows embodiments of the medical device in sectional side view and in cross-section.

FIG. 7a shows the prosthetic elongated portion 2201, also shown in FIG. 6h, when placed in the prosthetic replacement for the acetabulum 65 in a cross-sectional view, and in a side view. In the embodiment of FIG. 7a, the prosthetic replacement for the acetabulum surface comprises four extending portions 1823a,b,c,d clasping the prosthetic spherical portion 45 when implanted in the functional position in the hip joint. Each of the extending portions 1823a,b,c,d of the prosthetic replacement for the acetabulum has a rounded shape adapted to match corresponding rounded recesses of the elongated portion 2201. By the extending portions 2823a,b,c,d of the prosthetic acetabulum 65 entering the rounded recesses of the elongated portion 2201 the motion range of the prosthetic spherical portion 45 and the prosthetic elongated portion 2201 is further increased.

Figure 7B:
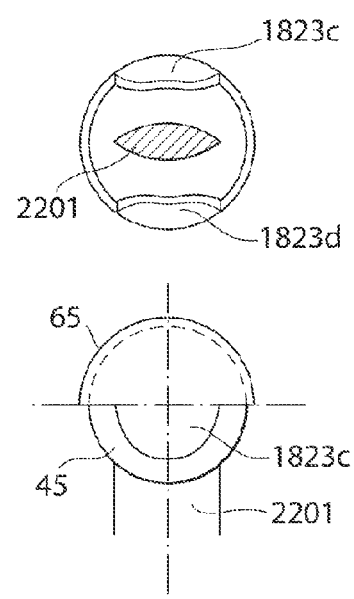

FIG. 7b shows the prosthetic elongated portion 2201, also shown in FIG. 6i, when placed in the prosthetic replacement for the acetabulum 65 in a cross-sectional view, and in a side view. In the embodiment of FIG. 7b, the prosthetic replacement for the acetabulum surface comprises two rounded extending portions 1823c,d clasping the prosthetic spherical portion 45 when implanted in the functional position in the hip joint. The cross section of the prosthetic elongated portion is a more narrow, elliptically shaped cross section which enables further movement of the prosthetic elongated portion in the narrow direction of the elliptically shaped elongated portion, where according to this embodiment, the extending portions of the prosthetic acetabulum is placed.

Figure 7C:
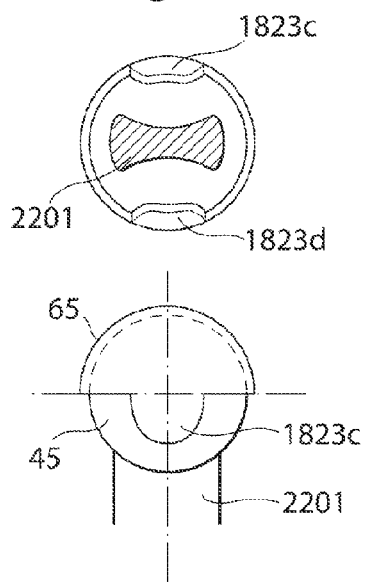

FIG. 7c shows the prosthetic elongated portion 2201, also shown in FIG. 6j, when placed in the prosthetic replacement for the acetabulum 65 in a cross-sectional view, and in a side view. In the embodiment of FIG. 7c, the prosthetic replacement for the acetabulum surface comprises two rounded extending portions 1823c,d clasping the prosthetic spherical portion 45 when implanted in the functional position in the hip joint. The two extending portions 1823c,d of the prosthetic replacement for the acetabulum has a rounded shape adapted to match corresponding rounded recesses of the elongated portion 2201. The shape of the prosthetic replacement for the acetabulum 65 is so adapted that the prosthetic elongated portion 2201 can move along a relatively large motion range whilst the extending portions still clasping the prosthetic spherical portion 45.

Figure 7D:
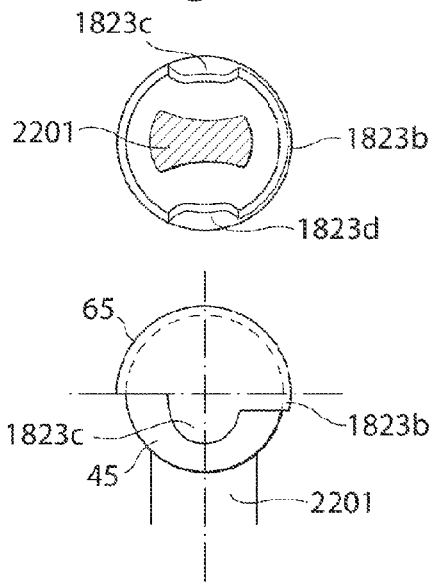

FIG. 7d shows the prosthetic elongated portion 2201, also shown in FIG. 6k, when placed in the prosthetic replacement for the acetabulum 65 in a cross-sectional view, and in a side view. In the embodiment of FIG. 7d, the prosthetic replacement for the acetabulum surface comprises two rounded extending portions 1823c,d, and one circumferentially elongated extending portion 1823b clasping the prosthetic spherical portion 45 when implanted in the functional position in the hip joint. The two extending portions 1823c,d of the prosthetic replacement for the acetabulum has a rounded shape adapted to match corresponding rounded recesses of the elongated portion 2201. The third extending portion 1823b is not extending as far as the two 1823c and 1823d, thus not limiting the motion range as much. The shape of the prosthetic replacement for the acetabulum 65 is so adapted that the prosthetic elongated portion 2201 can move along a relatively large motion range whilst the extending portions still clasping the prosthetic spherical portion 45.

Figure 8A:
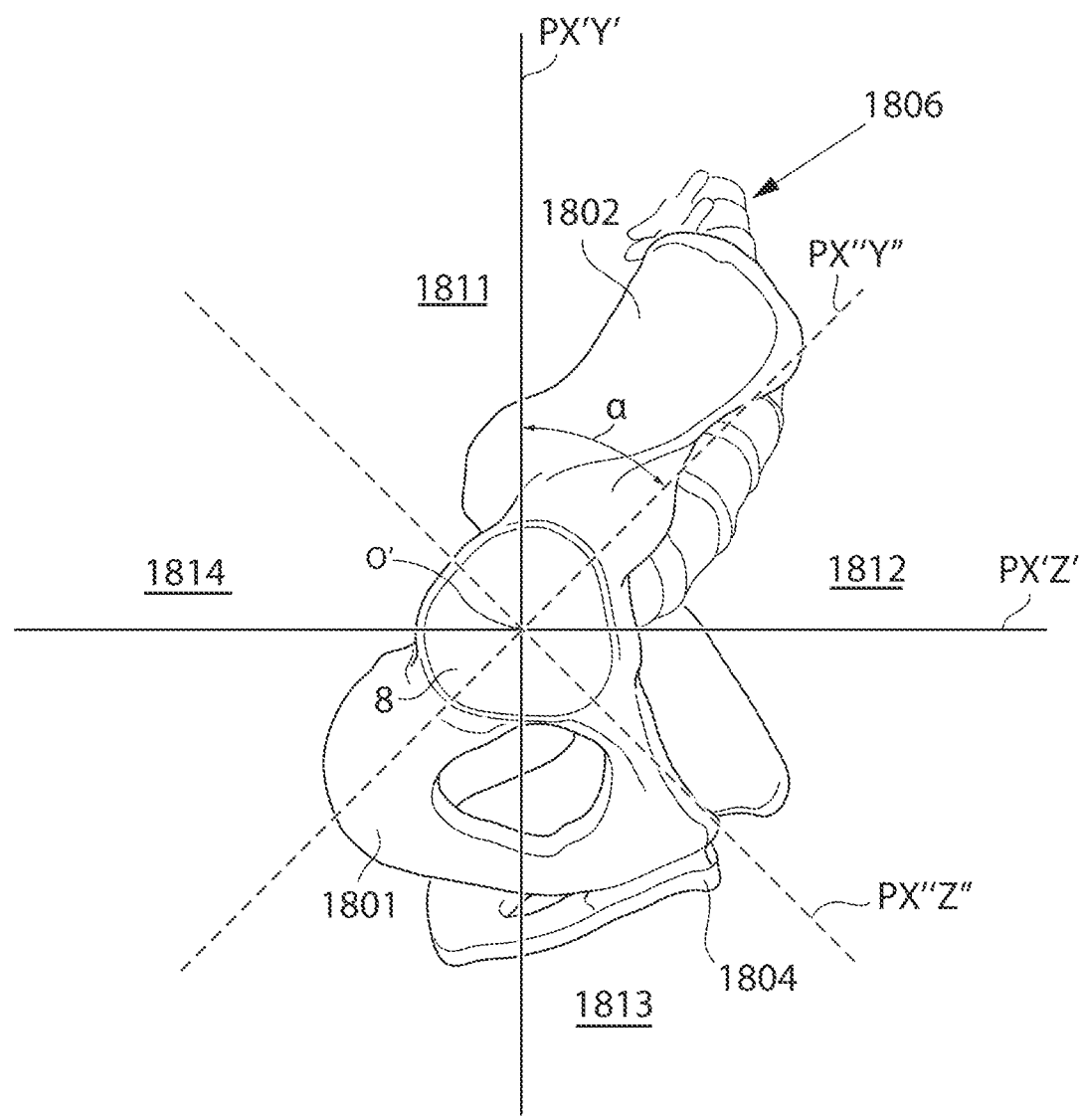
FIG. 8a shows pelvis in a lateral view.

FIG. 8a shows pelvis in the same view as FIG. 2b. Here the vertical and horizontal acetabulum planes PX'Y' and PX'Z' (further disclosed with reference to FIG. 2d) are shown in a strict plane view. Two further planes PX'Y' is introduced in FIG. 3, which planes are rotated an angle α of 45° clockwise. The planes PX'Y' and PX''Z'', in accordance with the planes PX'Y' and PX'Z' divides the acetabulum bowl into four different quadrants, being a proximal quadrant 1811, a frontal quadrant 1812, a distal quadrant 1813 and a dorsal quadrant 1814.

Figure 8B:
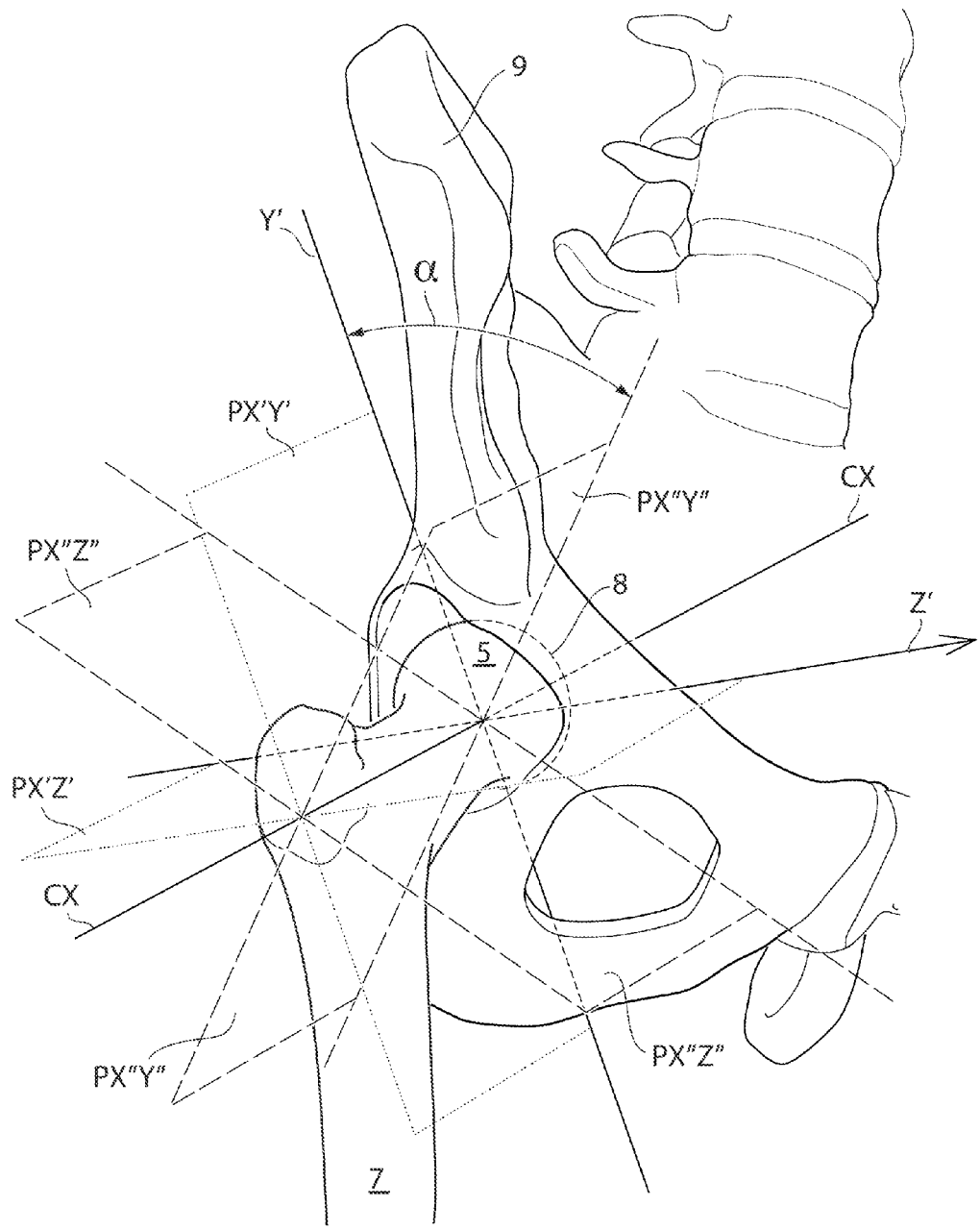
FIG. 8b shows the hip joint in section.

FIG. 8b shows a perspective view of the hip joint in section, displaying the horizontal and vertical planes PX'Y' and PX'Z' originating from the caput 5 and collum 6 center axis CX and dividing the caput 5 and collum 6 femur into quadrants. FIG. 8b further shows the planes PX''Y'' and PX''Z'' dividing the acetabulum bowl into four different quadrants, being a proximal quadrant 1811, a frontal quadrant 1812, a distal quadrant 1813 and a dorsal quadrant 1814, which is further disclosed with reference to FIG. 3a.

Figure 9A:
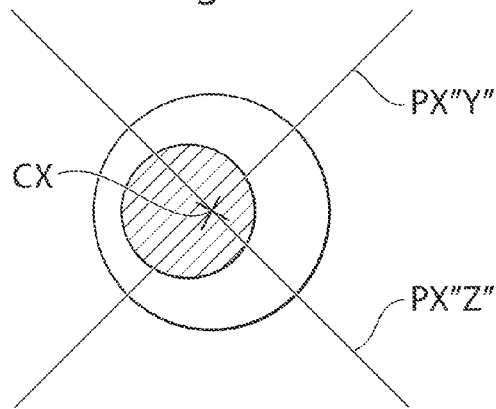
FIG. 9a-9c shows cross-sections of the medical device.

FIG. 9a shows a cross-section of an embodiment of the prosthetic elongated portion 2201, wherein said elongated portion is eccentrically placed in relation to the collum and caput center axis CX. The eccentric placement of the elongated portion 2201 places a large portion of the elongated portion 2201a in the dorsal quadrant, smaller portions of the elongated portions 2201b,d in the proximal and distal quadrants, respectively, and a smaller portion 2201c is placed in the frontal quadrant. The placing of a larger portion of the restricting portion of the elongated portion 2201 in the dorsal quadrant 1814 limits the motion range in the extension mostly. The movement range of the extension movements is less critical than for example flexion for every day activities, thus placing the major part of the elongated portion 2201a in the dorsal quadrant restrict the motion range needed in a less critical way. The eccentrically placed elongated portion is further disclosed with reference to FIGS. 6f and 6g.

Figure 9B:
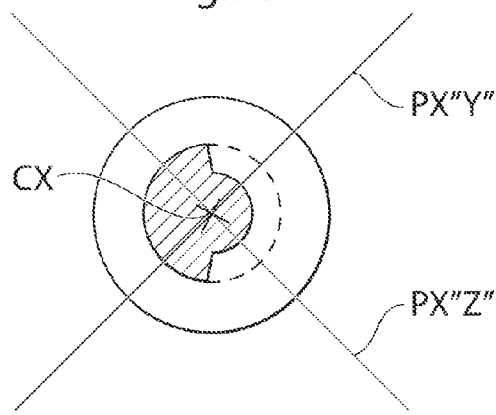

FIG. 9b shows a cross-section of an embodiment of the prosthetic elongated portion 2201, wherein said elongated portion comprises a recess 2203, mainly placed in the frontal 1812, proximal 1811 and distal 1813 quadrant, thus placing the major portion of the restricting portion of the elongated member in the dorsal quadrant 1814. The placing of a larger portion of the restricting portion of the elongated portion 2201 in the dorsal quadrant 1814 limits the motion range in the extension mostly. The movement range of the extension movements is less critical than for example flexion for every day activities, thus placing the major part of the elongated portion 2201a in the dorsal quadrant restrict the motion range needed in a less critical way. The elongated portion comprising a recess is further disclosed with reference to FIGS. 4b and 6b.

Figure 9C:
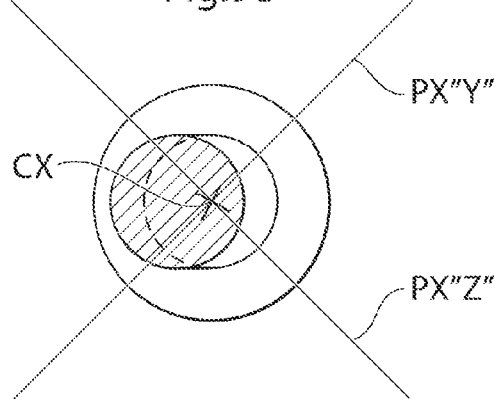

FIG. 9c shows a cross-section of an embodiment of the prosthetic elongated portion 2201, wherein said elongated portion 2201 is curved such that the connecting area between the prosthetic spherical portion 45 and the prosthetic elongated portion 2201 is eccentrically placed in relation to the caput and collum center axis CX, thus placing the major portion of the restricting portion of the elongated member 2201 in the dorsal quadrant 1814. The placing of a larger portion of the restricting portion of the elongated portion 2201 in the dorsal quadrant 1814 mainly limits the motion range in extension of the leg. The movement range of the extension movements is less critical than for example flexion for every day activities, thus placing the major part of the elongated portion 2201a in the dorsal quadrant restrict the motion range needed in a less critical way. The elongated portion comprising the curved elongated portion is further disclosed with reference to FIG. 4d.

Figure 10:
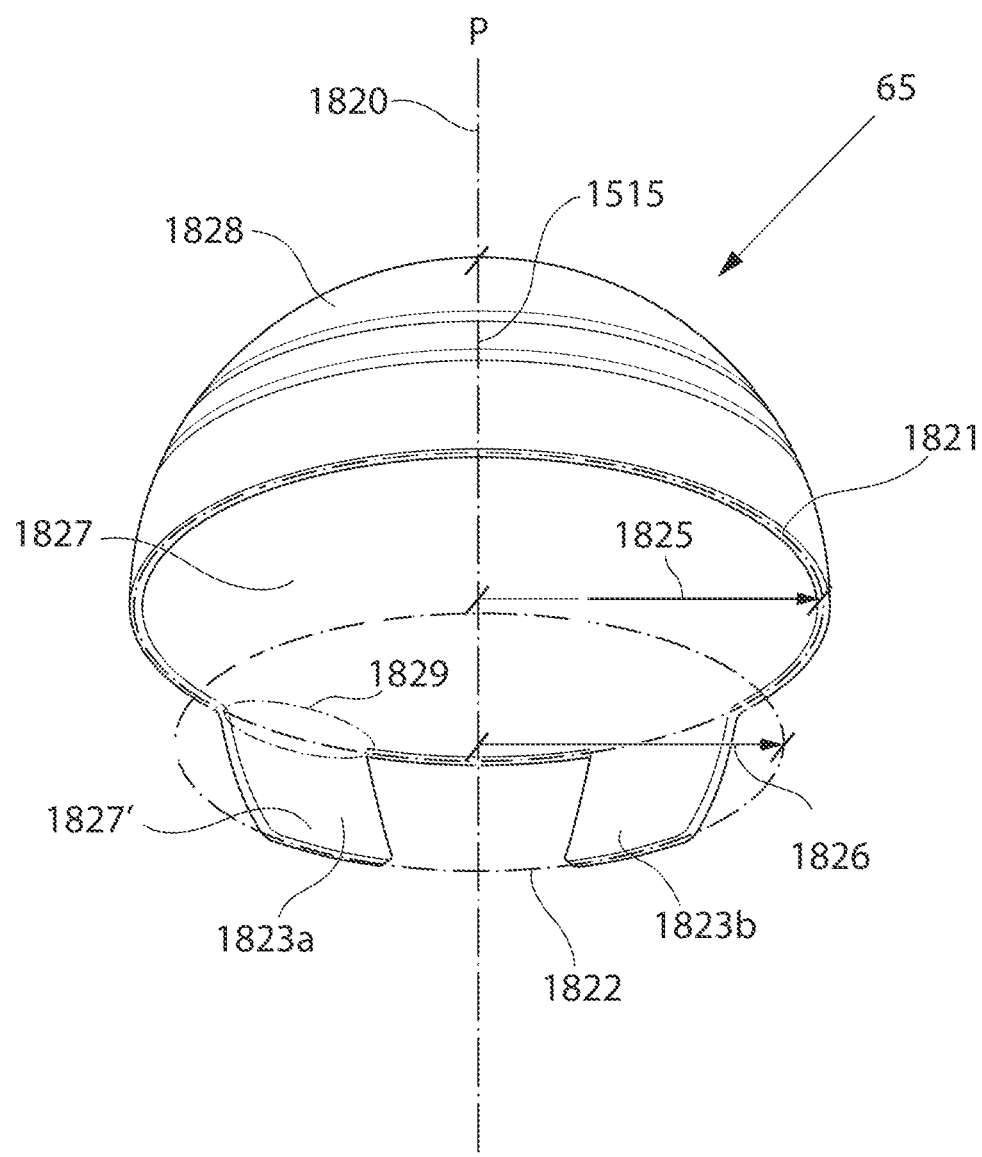
FIG. 10 shows a prosthetic replacement for the acetabulum, according to one embodiment.

FIG. 10 shows a medical device for implantation in a hip joint of a patient. The medical device is adapted to be fixated to the pelvic bone of the patient, for example by means of an adhesive, such as bone cement, or mechanical fixating members, such as orthopedic screws. The medical device comprises an inner 1827 and an outer 1828 surface. A contacting portion of the inner surface 1827 is spherical and faces the center of the hip joint, when the medical device is implanted. The inside of the medical device is adapted to receive a caput femur or a prosthetic replacement therefor having a spherical portion, and the spherical contacting portion of the inner surface 1827 is adapted to be in contact with a spherical portion of the outer surface of the caput femur or a prosthetic replacement therefor. The medical device, according to the embodiment shown in FIG. 4 comprises two extending portions 1823a,b, extending the contacting portion of the inner surface 1827' such that the extending portions 1823a,b clasps the spherical portion of caput femur or a prosthetic replacement therefor, for restraining the spherical portion in the medical device. The medical device is adapted to receive the prosthetic spherical portion, connected to the prosthetic elongated portion. The inner surface 1827 comprises an equator line 1821, being the largest circular circumference of the inner surface. The two extending portions passes beyond the equator line 1821, such that an end portion 1829 of the contacting portion, here being of the extending portion 1823b of the inner surface 1827, forms a circular extension line 1822 placed distal to the equator line 1821, when the medical device is implanted, and having a smaller circumference than the equator line 1821; thus a distance 1826 between a center axis P of the medical device and the extension line 1822 is shorter than a distance 1825 between the center axis P and the equator line 1821.

FIG. 11 shows the medical device described with reference to FIG. 10 when implanted. According to this embodiment the medical device is adapted to be fixated using orthopedic screws 1830, mechanically fixating the medical device to the pelvic bone 9, by the medical device comprising holes through which the screws 1830 are placed. In FIG. 5 the contacting portion of the inner surface 1827 has been placed in contact with the prosthetic spherical portion being connected to a the prosthetic elongated portion 2201, the prosthetic spherical 45 and elongated portions 2201 replacing the proximal portion of the femoral bone. The two extending portions 1823a and 1823b extending the contacting portion of the inner surface and clasping the spherical portion 45, for restraining the spherical portion in the medical device. The inner surface comprising the equator line 1821, and the extending portions 1823a,b passing beyond the equator line 1821 and comprising the more distal extension line 1822 having a smaller circumference than the equator line 1821. The more distal extension line 1822 being placed at a distance D1 form the equator line 1821. According to this embodiment the extension line 1822 is parallel to the equator line 1821, however this is not necessarily so in other embodiments. The extension portion 1823a according to the embodiment shown in FIG. 11 extends circumferentially along the equator line, a distance D2. Along another portion of the equator line, a distance D3, there are no extending portion, which enables the elongated portion 2201 to enter the space between the first and second extending portions 1823a,b which creates a larger movement range of the hip joint, for further increase of the movement range, the recess 2203 in the elongated portion 2201 is adapted for some section of the extending portion to enter the recess 2203.

The extending portion, according to any of the embodiments, adapted to clasp the prosthetic spherical portion, for restraining it the prosthetic acetabulum 65, could further be adapted to release the prosthetic spherical portion 45 when a large enough strain is placed on the joint. This feature enables the prosthetic spherical portion to be fixedly attached in the prosthetic acetabulum 65 in normal use, and be released from the prosthetic acetabulum, e.g. in case of an accident, thus reducing the risk of damaging the bodily structures, such as the femoral bone, or the fixations between bodily structures and prosthetic parts, such as the fixation between the femoral bone and a prosthetic stem to which the prosthetic collum and caput femur is fixated.

According to one embodiment, the extending elements, are placed such that the extending elements restrict the motion range minimally, or in ways which are not limiting the motion range used in everyday life. This is enabled through the placing of the extending portions, or the interaction between the extending portion and adaptations of the prosthetic elongated portion. The hip joint is a synovial ball and socket joint which permit a large motion range for allowing a plurality of different movements of the lower limb. From a neutral position, the following movements of the hip joint are normally possible: lateral or external rotation, 30° with the hip extended, 50° with the hip flexed, medial or internal rotation 40°, extension or retroversion 20°, flexion or anteversion 140°, abduction 50° with hip extended, 80° with hip flexed, adduction 30° with hip extended, 20° with hip flexed. In the movement ranges of abduction and adduction the depth of the acetabulum bowl and thus the extending portions does not restrict the motion range in a critical way since the motion range of the normal hip is restricted in these movements, in normally agile persons, by the muscles, tenors and ligaments surrounding the hip joint.

Figure 12A:
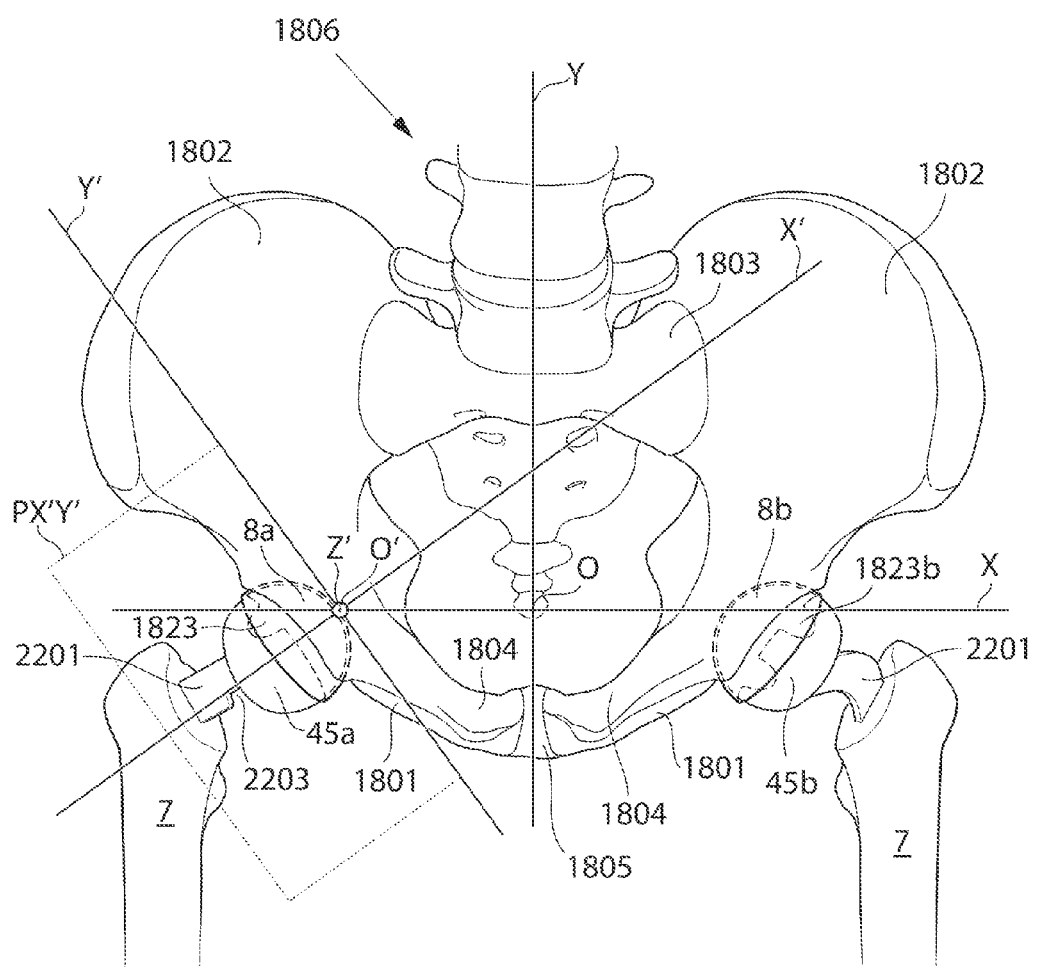
FIG. 12a shows the pelvic region in a frontal view.

FIG. 12a shows a frontal view of pubis and the proximal portions of the femoral bones 7 when two embodiments prosthetic replacement for the acetabulum 65 has been implanted in the hip joint. The prosthetic replacements for the acetabulum shown comprises one extending portion 1823, here placed dorsal to the vertical acetabulum plane PX'Y', thus only partially limiting abduction in far excess of 50°. According to the embodiment shown, the extending portion 1823 extends circumferentially along the equator line 1821 about 1/10 of the length of the equator line 1821, however in other embodiment the extending portion 1823 extends along as much as half of the length of the equator line 1821, and in other embodiments the extending portion 1823 extends as lithe as about 1/30 of the length of the equator line 1821. The prosthetic replacement for the acetabulum placed in the left acetabulum 8b comprises two extending portions 1823a,b, both being placed dorsal the corresponding vertical acetabulum plane PX'Y' of the left acetabulum (not shown), thus limiting the motion range of the hip joint in a non restrictive way, in relation to everyday activities. In both the right and left embodiment the extending portions 1823 extends discontinuously along the equator line 1821 thus enabling the elongated portion 2201 to partially be placed between the equator line and the extension line, and in the left embodiment, be placed between the extending portions 1823a,b thus entering the cavity between the extending portions 1823a,b. The recess 2203 of the prosthetic elongated portion 2201 implanted in the right hip joint is radially placed, in relation to the caput and collum center axis, such that the a section of the prosthetic elongated portion 2201, can enter the recess for further increasing the movement range of the elongated 2201 and spherical 45a portion in relation to the prosthetic acetabulum surface 65. The curving of the prosthetic elongated portion 2201 implanted in the left hip joint is radially placed, in relation to the caput and collum center axis, for further increasing the movement range of the elongated 2201 and spherical 45b portion in relation to the prosthetic acetabulum surface 65.

Figure 12B:
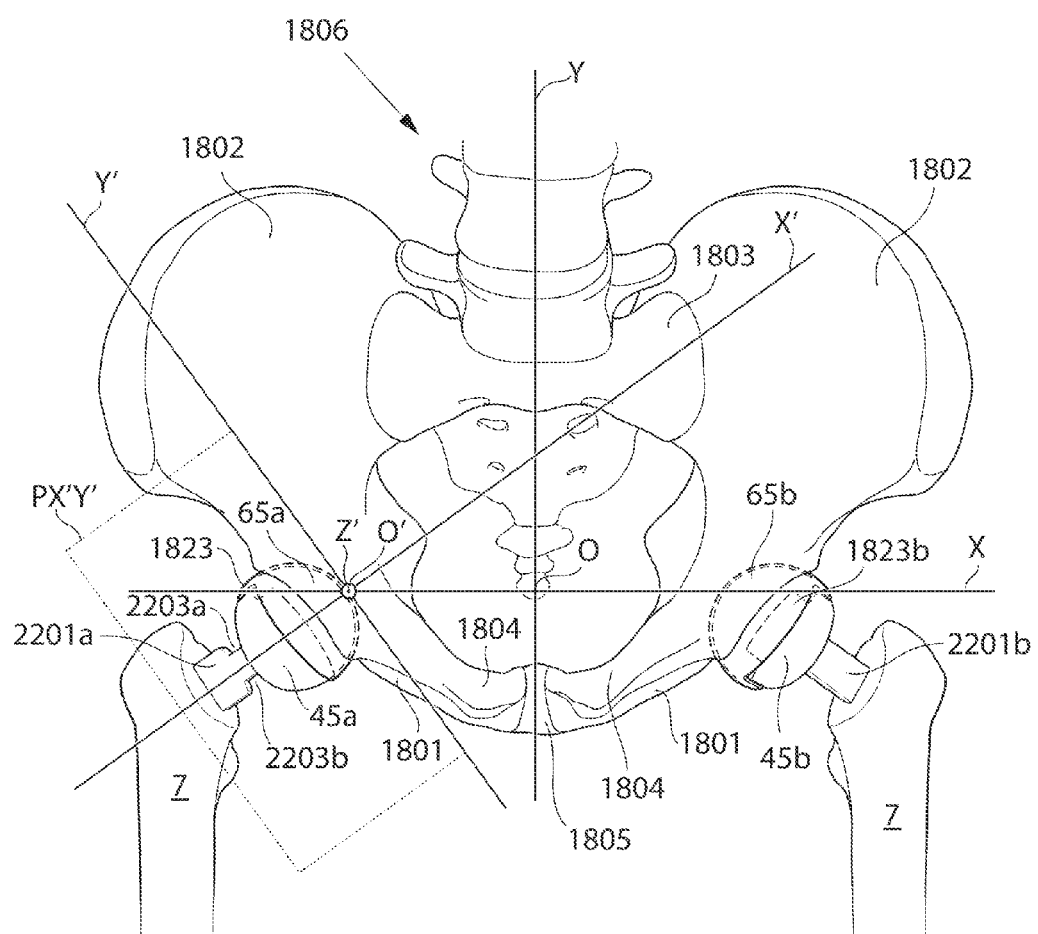
FIG. 12b shows the pelvic region in a frontal view.

FIG. 12b shows a frontal view of pubis and the proximal portions of the femoral bones 7, when two further embodiments of the prosthetic replacements have been implanted. The embodiment shown placed on the right side is an embodiment in which the prosthetic elongated portion 2201a adapted to replace the collum femur comprises a first 2203a and second 2203b recess placed at the restricting portion of the elongated portion 2201a. The prosthetic elongated portion is connected to a prosthetic spherical portion 45a which is restrained in a prosthetic replacement for the acetabulum 65a fixated to the pelvic bone. The prosthetic replacement for the acetabulum 65a comprises extending portions 1823 clasping the prosthetic spherical portion 45a and thus restraining the spherical portion if the prosthetic replacement for the acetabulum 65a. The extending portions 1823 is placed in the proximal quadrant, thus limiting the motion range of the hip joint in a nonrestrictive way, in relation to everyday activities. According to the embodiment shown, the extending portion 1823 extends circumferentially along the equator line 1821 about 1/10 of the length of the equator line 1821, however in other embodiments the extending portion 1823 extends along as much as half of the length of the equator line 1821, and in other embodiments the extending portion 1823 extends as lithe as about 1/30 of the length of the equator line 1821. The prosthetic elongated portion 2201b shown placed in the left hip joint comprises a narrow portion connected to the prosthetic spherical portion 45b. The narrow portion enables a relatively large motion range in relation to the prosthetic replacement for the acetabulum 65b, even though the prosthetic replacement for the acetabulum comprises extending portions 1823a,b extending beyond the equator line of the prosthetic spherical portion 45b, thus clasping the spherical portion and restraining it in a fixated position.

Figure 13:
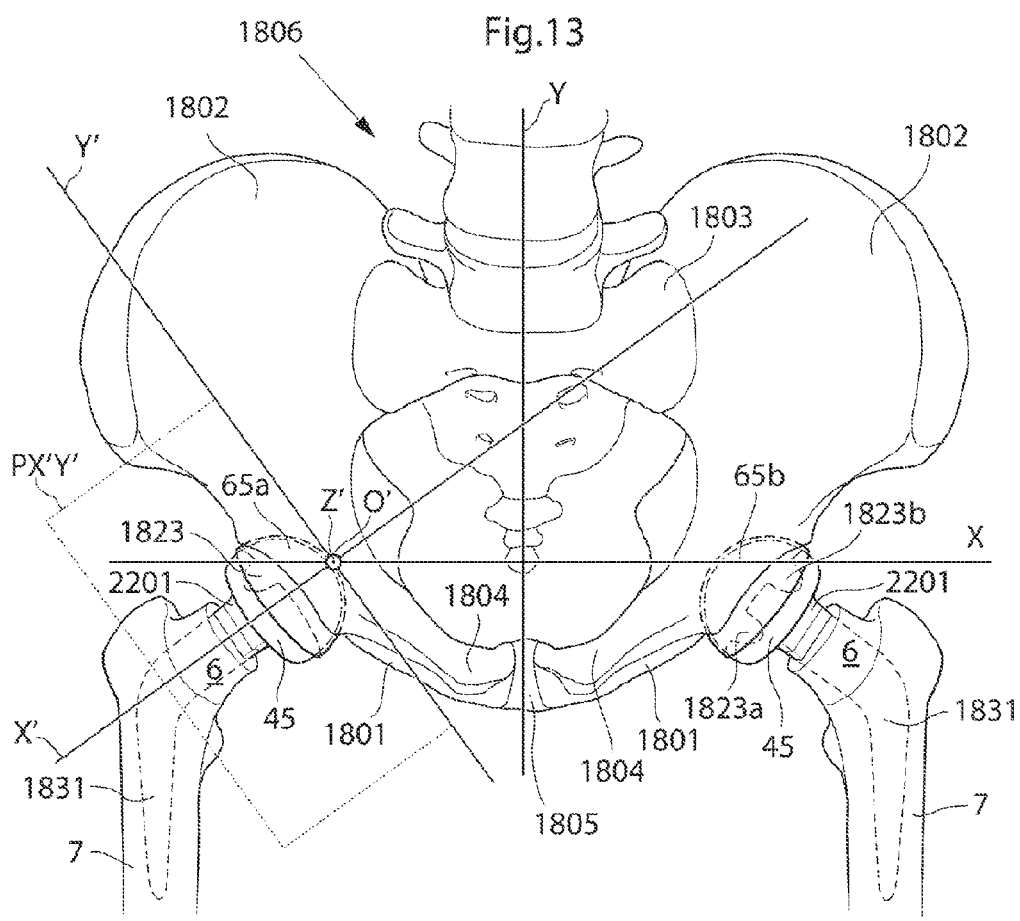
FIG. 13 shows the pelvic region in a frontal view.

FIG. 13 shows the pelvis and the proximal portions of the femoral bones 7 including the embodiment of FIG. 12a, with the difference that the natural caput femur and a portion of the natural collum femur has been replaced by a prosthetic spherical portion 45 and a prosthetic elongated portion 2201. The prosthesis further comprises a prosthetic stem 1831 adapted to be placed inside and fixated to the femoral bone, either using bone cement or by the surface of the stem being adapted to facilitate the growth-in of bone, thus fixating the stem. The prosthetic elongated portion 2201 is here coordinated with the extending portions 1823 of the prosthetic replacement for the acetabulum 65a,b for further improving the motion range of the hip joint, or not limiting the natural motion range of the hip joint.

Figure 14:
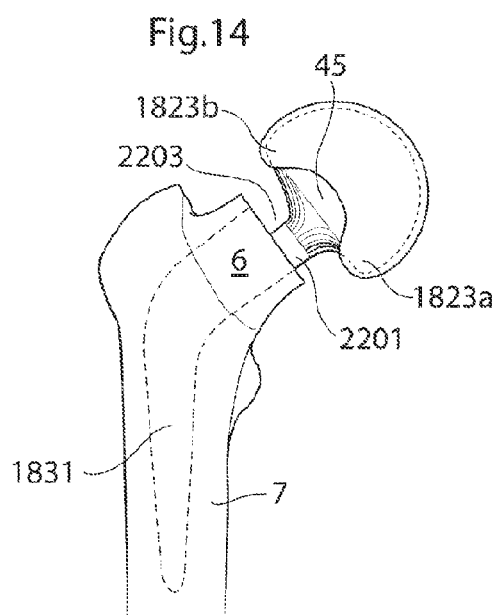
FIG. 14 shows a medical device placed in the femoral bone.

FIG. 14 shows the medical device according to an embodiment in which the medical device comprises two extending portions 1823a,b. The medical device is placed on a prosthetic elongated portion 2201, to which a prosthetic spherical portion 45 is attached. The prosthesis further comprises a stem 1831 which is adapted to be fixated inside of the femoral bone 7. The prosthetic elongated member 2201 is here adapted to further improve the motion range of the hip joint, or not limiting the natural motion range of the hip joint, by the prosthetic elongated portion 2201 comprising a recess 2203 in which the extending portions 1823 can enter.

Figure 15A:
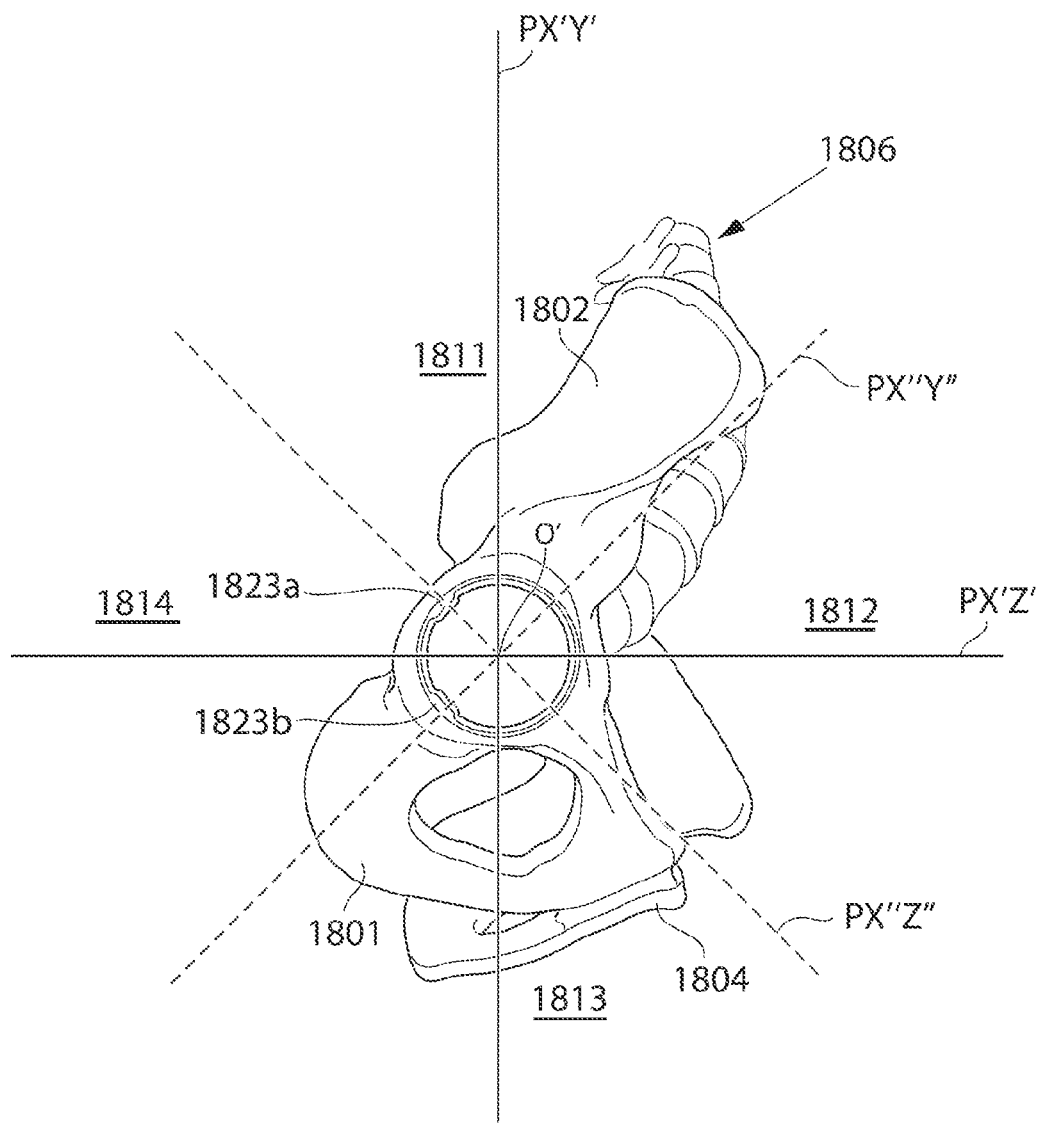
FIG. 15a shows the pelvis in a lateral view.

FIG. 15a shows the pelvis in a lateral view, the prosthetic replacement for the acetabulum 65 comprises two extending portions 1823a,b, both extending circumferentially along the equator line (as disclosed in for example FIG. 5) dorsal to the caudal-cranial axis Y and being adapted to clasp the caput femur or a prosthetic replacement therefor. The extending portions 1823a,b extending dorsal to the caudal-cranial axis Y and thus reducing the limiting effect that the extending portions 1823a,b, have on the motion range of the hip joint According to the embodiment shown in FIG. 15a the extending portion 1823a, placed proximally in the acetabulum, extends circumferentially a distance of about ¼ of the length of the equator line, and the extending portion 1823b, placed distally in the acetabulum, extends circumferentially a distance of about 1/10 of the length of the equator line, however it is equally conceivable that this relationship is the other way around, or that any of the extending portions circumferentially extends a distance of as much as half of the length of the equator line, thus extending the entire distance of the equator line being dorsal to the vertical acetabulum plane PX'Y', or that any of the extending portions 1823a,b extends a distance being as little as 1/30 of the distance of the equator line. According to the embodiment shown in FIG. 15a, the first extending portion 1823a extends in distal-lateral direction from the acetabulum, and the second extending portion 1823b extends medially towards foramen obturatum.

Figure 15B:
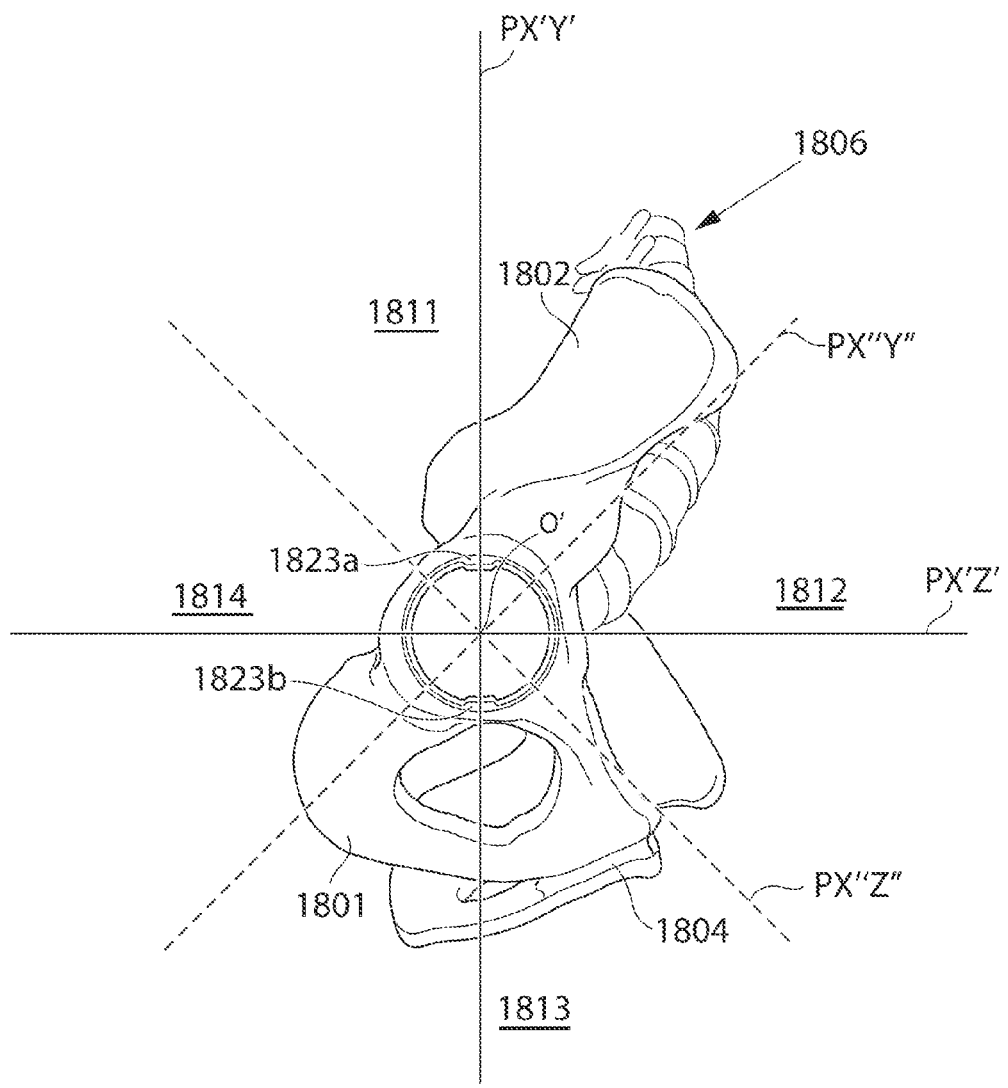
FIG. 15b shows the pelvis in a lateral view.

FIG. 15b shows the pelvis in a lateral view, the prosthetic replacement for the acetabulum 65 comprises two extending portions 1823a,b, the two extending portions 1823a,b extends in the proximal quadrant 1811 and the distal quadrant 1813, respectively.

There are multiple ways in which the extending portions 1823 can be adapted to reduce the effects that the extensions have on the motion range of the hip joint.

Figure 16:
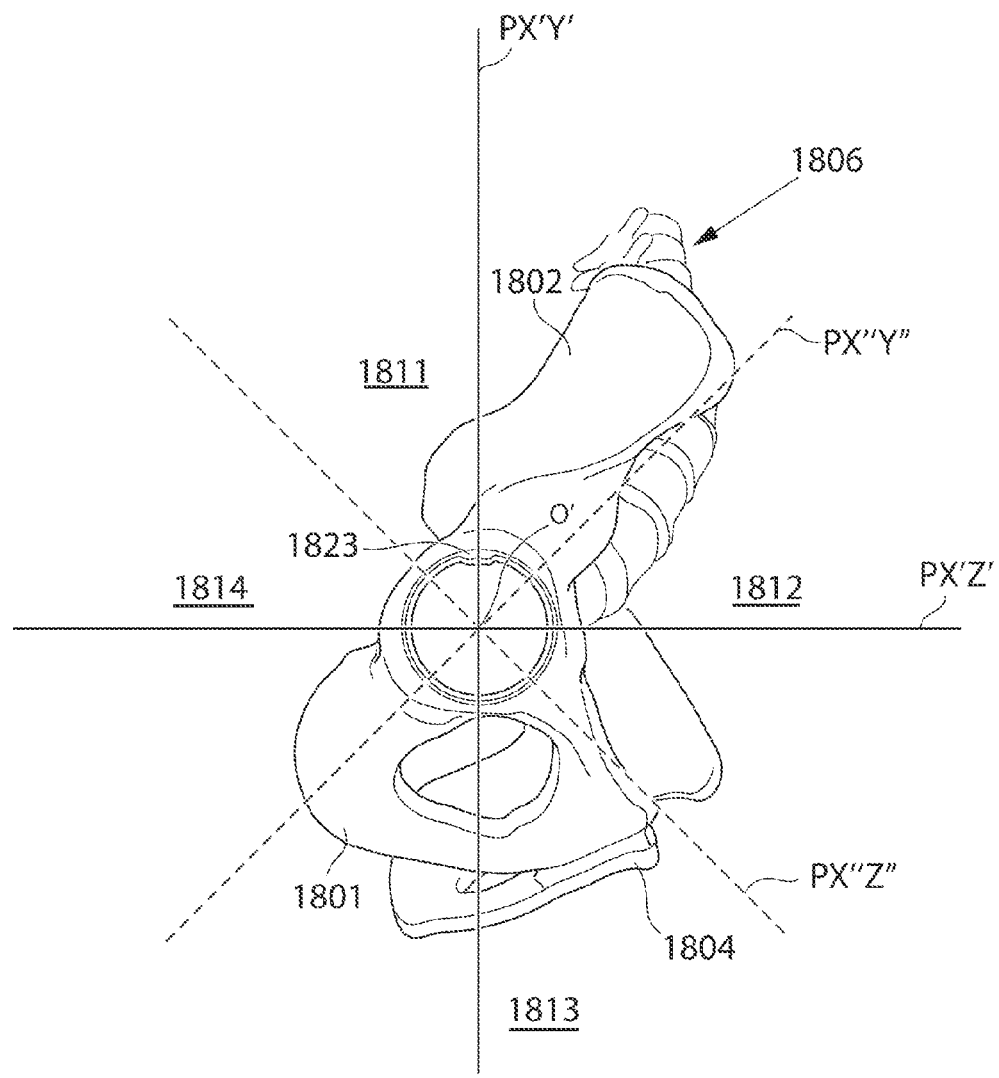
FIG. 16 shows the pelvis in a lateral view.

FIG. 16 shows the pelvis in a lateral view, the prosthetic replacement for the acetabulum 65 shown comprises one extending portion 1823 extending and being adapted to clasp the caput femur, or a prosthetic replacement therefor. The extending portion 1823 extends circumferentially along the equator line within the proximal quadrant 1811, which is further disclosed with reference to FIG. 3. According to the embodiment shown in FIG. 10, the extending portion 1823 extends in distal-lateral direction from the acetabulum.

Figure 17:
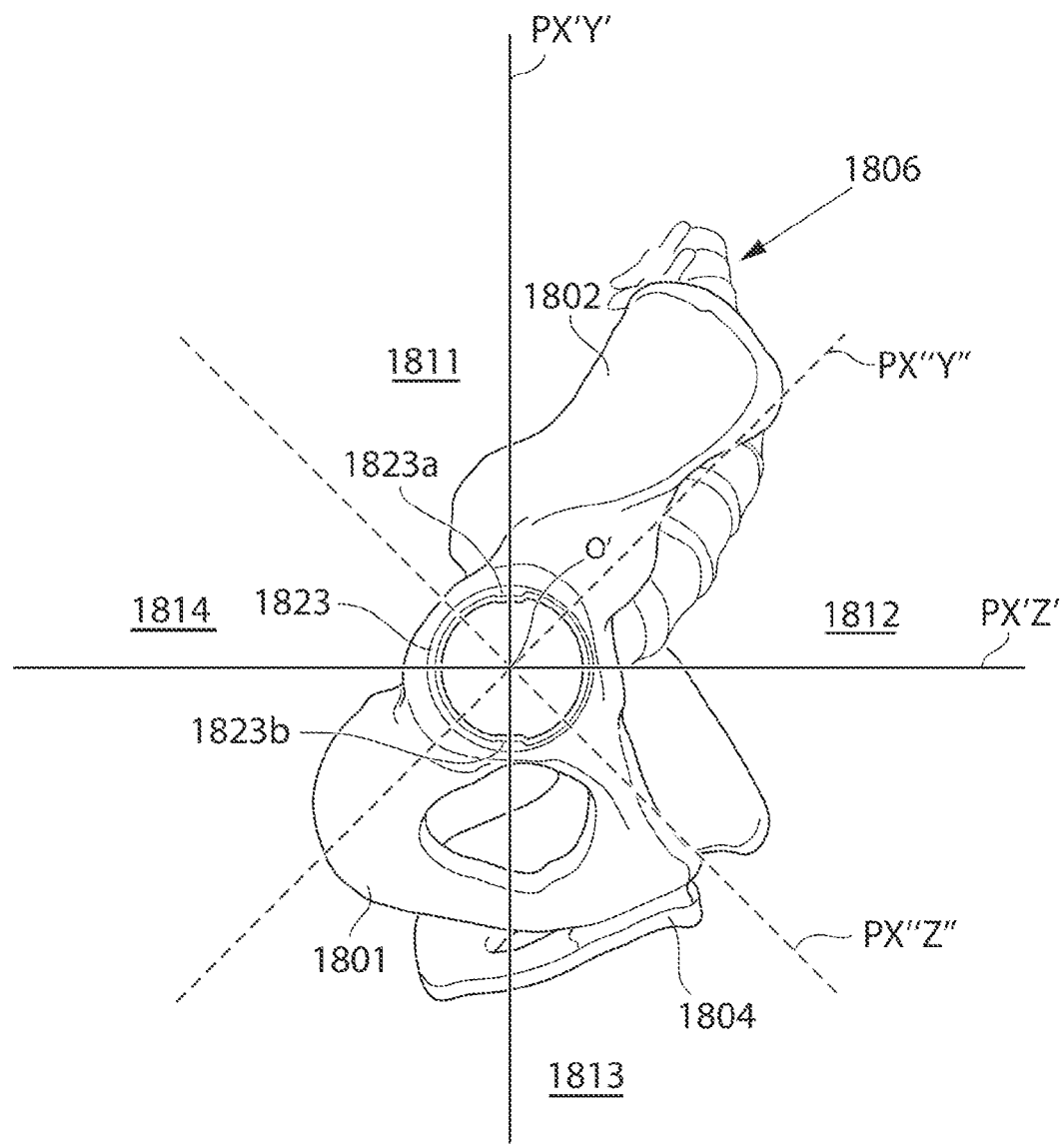
FIG. 17 shows the pelvis in a lateral view.

FIG. 17 shows the pelvis in a lateral view, the prosthetic replacement for the acetabulum 65 shown comprises a continuously extending portion 1823 with two extending portions 1823a and 1823b extending further in relation to the average extension of the extending portion. The entire extending portion is placed in the proximal, distal and dorsal quadrants and the extending portions 1823a,b extending further than the average extension of the extending portion 1823 extends in the proximal and distal quadrant.

Figure 18:
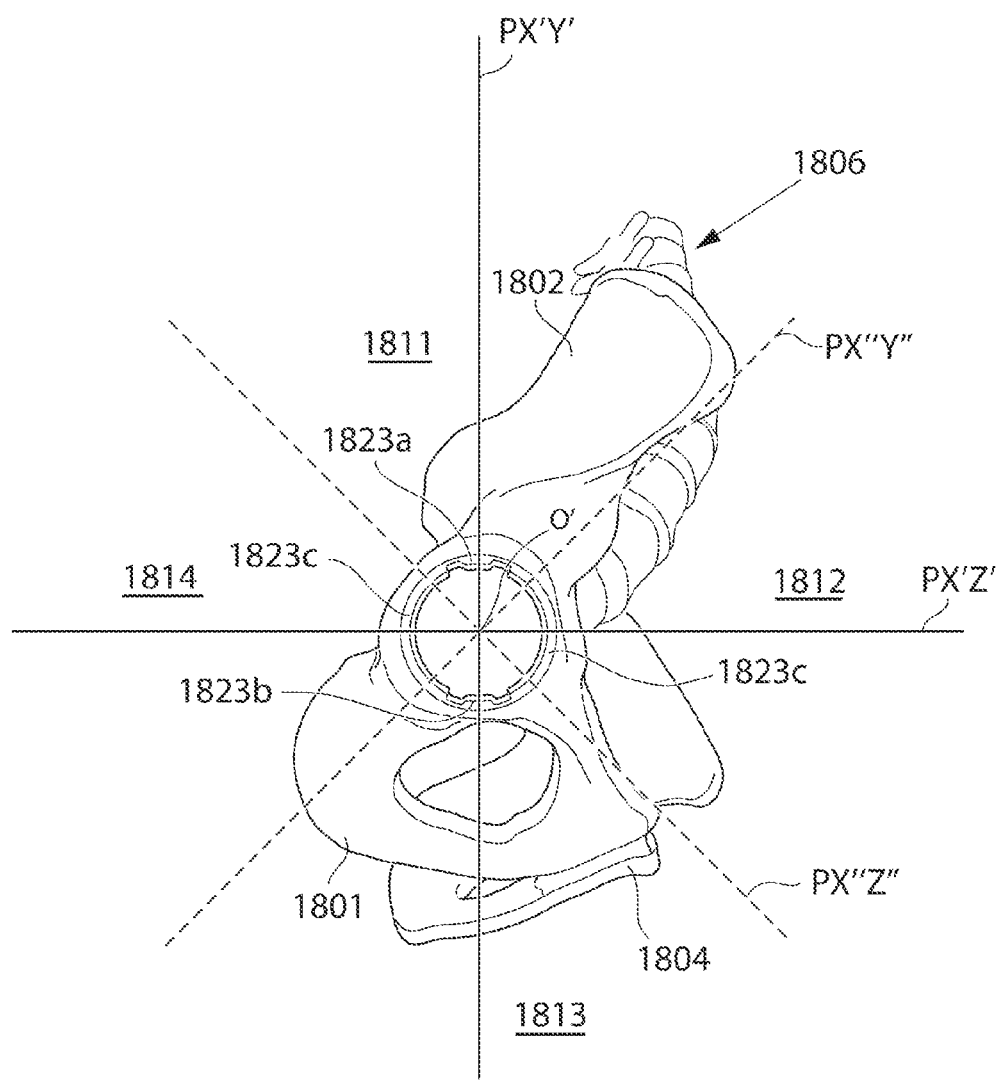
FIG. 18 shows the pelvis in a lateral view.

FIG. 18 shows the pelvis in a lateral view, the prosthetic replacement for the acetabulum 65 shown comprises four extending portions 1823a,b,c,d, wherein the first 1823a and second 1823b extending portions extends in the proximal and distal quadrant, respectively, thus the first extending portion 1823a extending in distal-lateral direction from the acetabulum, and the second extending portion 1823b extending medially towards foramen obturatum. The third extending portion 1823c extending in the frontal quadrant 1812, out from the acetabulum in dorsal direction, extends less than the first and second extending portion, since extending portions 1823c in the frontal quadrant is more limiting to the normal motion range of the hip joint. The fourth extending portion 1823d extends in the dorsal quadrant in accordance with the third extending portion 1823c do not extend as far as the first and second extending portions.

Figure 19:
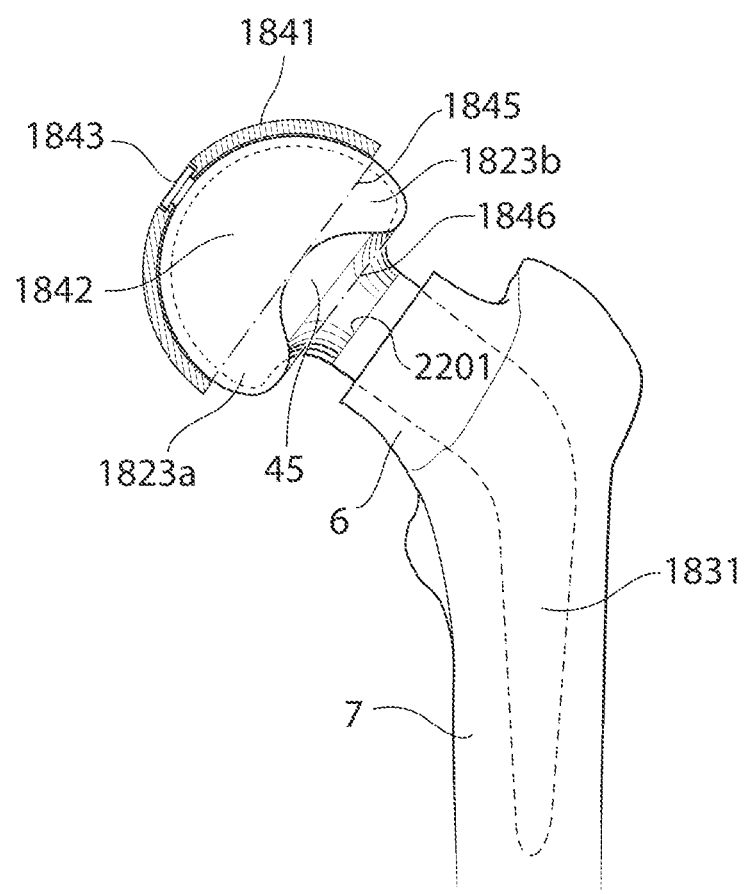
FIG. 19 shows a medical device placed in the femoral bone.

FIG. 19 shows an alternative embodiment of the prosthetic replacement for the acetabulum 65. In the alternative embodiment, the prosthetic replacement for the acetabulum 65 comprises a first part 1841 adapted to be fixated to the pelvic bone of the patient. The first part comprises an inner contacting surface adapted to be in movable connection with an outer contacting surface of a second part 1842. The second part 1842 is rotatably fixated to the first part 1841 by a rotatable connecting member 1843. An outer contacting surface of a prosthetic spherical portion 45 is adapted to be placed in contact with the inner surface of the second part 1842 and be movable in multiple directions, thus replicating the natural ball and socket joint of the hip. The second part 1842 comprises two extending portions 1823a,b extending beyond the equator line 1845 of the second part 1842. The extending portions 1823a,b extends longitudinally discontinuously along the equator line, thus creating an area between the extending portions, in which area a portion of the prosthetic collum femur can be placed, thus being placed partially between the equator line 1845 and the extension line 1846. The construction shown in FIG. 13 enables the second part 1842 to rotate if the prosthetic elongated portion 2201 engages the extending portions 1823a,b, which are sloped for this purpose. This way the second part 1842 are always placed such that the prosthetic elongated portion 2201 can be placed partially between equator line 1845 and the extension line 1846, which creates an optimal range of movement whilst the second part clasps the prosthetic spherical portion 45, and thus restricting the spherical portion 45 in the second part 1842 of the prosthetic replacement for the acetabulum 65.

Figure 20A:
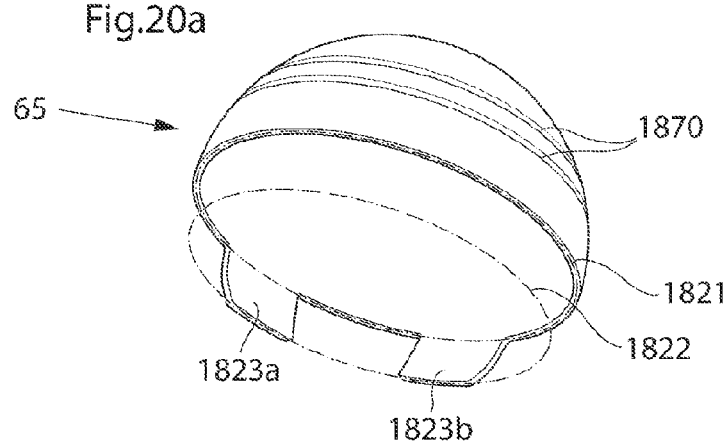

FIG. 20a shows the prosthetic replacement for the acetabulum 65 in a perspective view from below according to one embodiment. In this embodiment the prosthetic replacement for the acetabulum 65 comprises two extending portions 1823a, b. The prosthetic replacement for the acetabulum 65 is according to this embodiment adapted to be fixated to the pelvic bone by means of an adhesive which is adapted to be placed in connection with the adhesive recesses 1870 of the outer surface of the prosthetic replacement for the acetabulum 65.

Figure 20B:
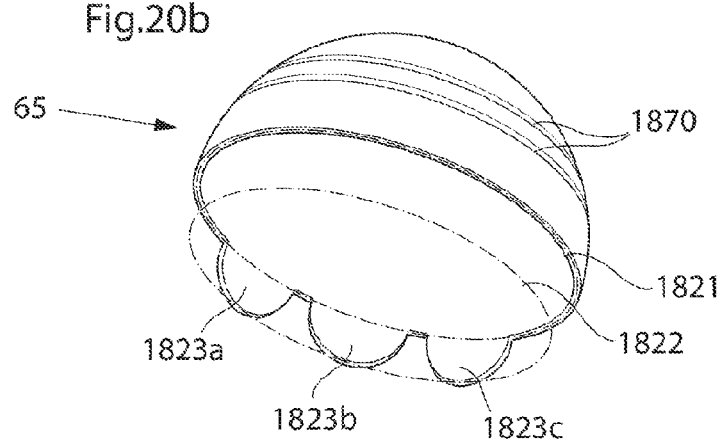

FIG. 20b shows a prosthetic replacement for the acetabulum 65 similar to the prosthetic replacement for the acetabulum 65 disclosed with reference to FIG. 20a, but with the difference that it comprises three equally extending portions 1823a,b,c.

Figure 20C:
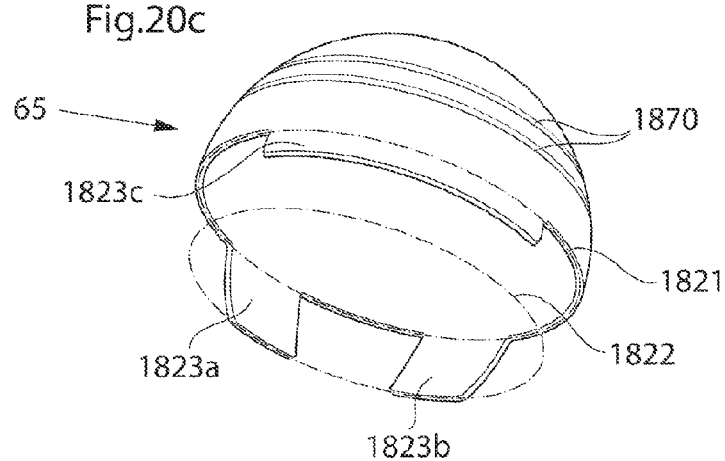

FIG. 20c shows a prosthetic replacement for the acetabulum 65, similar to the prosthetic replacement for the acetabulum 65 disclosed with reference to FIG. 20a, but with the difference that it comprises two equally extending portions 1823a,b and one less extending portion 1823c.

FIG. 20d shows a prosthetic replacement for the acetabulum 65 similar to the prosthetic replacement for the acetabulum 65 disclosed with reference to FIG. 20a, but with the difference that it comprises four equally extending portions 1823a,b,c,d.

FIG. 20e shows a prosthetic replacement for the acetabulum 65 similar to the prosthetic replacement for the acetabulum 65 disclosed with reference to FIG. 20a, but with the difference that the two extending portions are placed further from each other, and thus being adapted to be placed in the proximal and distal quadrant, when implanted.

FIG. 20f shows a prosthetic replacement for the acetabulum 65 similar to the prosthetic replacement for the acetabulum 65 disclosed with reference to FIG. 20a, but further comprising a less extending portion 1823c placed between the first and second extending portions 1823a,b.

The extending portions of the prosthetic replacement for the acetabulum 65 which have been described could be made from an elastic material, enabling the extending portions to pass onto the a prosthetic spherical portion, according to any of the embodiments herein.

FIG. 21a shows the prosthetic elongated portion 2201, also shown in FIG. 7a, when placed in the prosthetic replacement for the acetabulum 65 in a cross-sectional view, and in a side view. In the embodiment of FIG. 21a, the prosthetic replacement for the acetabulum surface comprises four extending portions 1823a,b,c,d clasping the prosthetic spherical portion 45 when implanted in the functional position in the hip joint. Each of the extending portions 1823a, b,c,d of the prosthetic replacement for the acetabulum has a rounded shape adapted to match corresponding rounded recesses of the elongated portion 2201. By the extending portions 2823a,b,c,d of the prosthetic acetabulum 65 entering the rounded recesses of the elongated portion 2201 the motion range of the prosthetic spherical portion 45 and the prosthetic elongated portion 2201 is further increased. According to the embodiment shown in FIG. 21a, the elongated portion 2201 is placed centered in relation to the collum and caput center axis, such that the an equal portion of the elongated portion is placed in the proximal 1811, distal 1813, frontal 1812 and dorsal 1814 quadrant, respectively.

FIG. 21*b* shows the prosthetic elongated portion 2201, also shown in FIG. 7*b*, when placed in the prosthetic replacement for the acetabulum 65 in a cross-sectional view, and in a side view. In the embodiment of FIG. 21*b*, the prosthetic replacement for the acetabulum surface comprises two rounded extending portions 1823*c,d* clasping the prosthetic spherical portion 45 when implanted in the functional position in the hip joint. The cross section of the prosthetic elongated portion is a more narrow, elliptically shaped cross section which enables further movement of the prosthetic elongated portion in the narrow direction of the elliptically shaped elongated portion, where according to this embodiment, the extending portions of the prosthetic acetabulum is placed. The prosthetic replacement for the acetabulum 65 and the prosthetic elongated portion 2201 are oriented in relation to the acetabulum, such that the extending portions 1823*c,d* are placed in the proximal 1811 and distal 1813 quadrant, and the major parts of the elongated portion 2201 are placed in the frontal 1812 and dorsal 1814 quadrant, while only minor parts are placed in the proximal 1811 and distal 1813 quadrants. This configuration enables the prosthetic replacement for the acetabulum 65 to have extending portions 1823*c,d*, and the elongated portion to have a relatively large cross-section without restricting the motion range of the hip joint in excess of the restriction of a natural hip joint, in any direction.

FIG. 21*c* shows the prosthetic elongated portion 2201, also shown in FIG. 7*c*, when placed in the prosthetic replacement for the acetabulum 65 in a cross-sectional view, and in a side view. In the embodiment of FIG. 21*c*, the prosthetic replacement for the acetabulum surface comprises two rounded extending portions 1823*c,d* clasping the prosthetic spherical portion 45 when implanted in the functional position in the hip joint. The two extending portions 1823*c,d* of the prosthetic replacement for the acetabulum 65 has a rounded shape adapted to match corresponding rounded recesses of the elongated portion 2201. The shape of the prosthetic replacement for the acetabulum 65 is so adapted that the prosthetic elongated portion 2201 can move along a relatively large motion range whilst the extending portions still clasping the prosthetic spherical portion 45. This configuration enables the prosthetic replacement for the acetabulum 65 to have extending portions 1823*c,d*, and the elongated portion to have a relatively large cross-section without restricting the motion range of the hip joint in excess of the restriction of a natural hip joint, in any direction.

FIG. 21*d* shows the prosthetic elongated portion 2201, also shown in FIG. 7*d*, when placed in the prosthetic replacement for the acetabulum 65 in a cross-sectional view, and in a side view. In the embodiment of FIG. 21*d*, the prosthetic replacement for the acetabulum 65 comprises two rounded extending portions 1823*c,d*, and one circumferentially elongated extending portion 1823*b* clasping the prosthetic spherical portion 45 when implanted in the functional position in the hip joint. The two extending portions 1823*c,d* of the prosthetic replacement for the acetabulum 65 has a rounded shape adapted to match corresponding rounded recesses of the elongated portion 2201. The third extending portion 1823*b* is not extending as far as the two 1823*c* and 1823*d*, thus not limiting the motion range as much. The shape of the prosthetic replacement for the acetabulum 65 is so adapted that the prosthetic elongated portion 2201 can move along a relatively large motion range whilst the extending portions still clasping the prosthetic spherical portion 45. The prosthetic replacement for the acetabulum 65 and the prosthetic elongated portion 2201 are oriented in relation to the acetabulum, such that the extending portions 1823*c,d* are placed in the proximal 1811 and distal 1813 quadrant, where only minor part of the elongated portion 2201 are placed. A large portion if the elongated portion 2201 is placed in the dorsal quadrant 1814, where no extending portion is present, while a smaller, but still relatively large portion of the elongated portion 2201 is placed in the frontal 1812 quadrants, where a less extending portion is placed. This configuration enables the prosthetic replacement for the acetabulum 65 to have extending portions 1823*c,b,d* in three directions, creating a very stable configuration, whilst still enabling the elongated portion to have a relatively large cross-section without restricting the motion range of the hip joint in far excess of the restriction of a natural hip joint.

Examples of embodiments of different adaptations of the elongated portion, alone, or adaptations in conjunction with corresponding adaptations of the prosthetic replacement for the acetabulum have been shown. The placement of the elongated member in relation to the prosthetic replacement for the acetabulum is critical to the obtained motion range for a prosthetic hip joint comprising a prosthetic replacement for the acetabulum with portions extending beyond the equator of the spherical portion clasped therein. According to some embodiments $\frac{1}{10}$ of the cross section of the restricting portion of the elongated member is placed in the proximal and distal quadrants, whereas $\frac{9}{10}$ are placed in the frontal and dorsal quadrants, which $\frac{9}{10}$ could be equally distributed between the two quadrants, or a major part, such as $\frac{5}{10}$ could be placed in the dorsal quadrant and $\frac{4}{10}$ could be placed in the frontal quadrants, however it is equally conceivable that it is the other way around depending of the design of the prosthetic replacement for the acetabulum. In embodiments comprising deep recesses or adaptations, or in embodiments where the restricting portion of the elongated portion is placed eccentrically in relation to the collum and caput center axis, as little as $\frac{9}{10}$ of the elongated portion could be placed in a particular quadrant and from that the entire range from $\frac{1}{10}$-$10/10$ of the restricting portion of the elongated portion could be placed in any of the quadrants to obtain an advantageous motion range, all depending on the placement of the prosthetic replacement for the acetabulum in relation to the pelvic bone, and in particular the extending portions of the prosthetic replacement for the acetabulum.

The medical device according to any of the embodiments could comprise at least one material selected from a group consisting of polytetrafluoroethylene (PTFE), perfluoroalkoxy (PFA) and fluorinated ethylene propylene (FEP). It is furthermore conceivable that the material comprises a metal alloy, such as cobalt-chromium-molybdenum or titanium or stainless steel, or polyethylene, such as cross-linked polyethylene or gas sterilized polyethylene. The use of ceramic material is also conceivable, in the contacting surfaces or the entire medical device such as zirconium or zirconium dioxide ceramics or alumina ceramics. The part of the medical device in contact with human bone for fixation of the medical device to human bone could comprise a poorhouse structure which could be a porous micro or nano-structure adapted to promote the growth-in of human bone in the medical device for fixating the medical device. The porous structure could be achieved by applying a hydroxy-apatite (HA) coating, or a rough open-pored titanium coating, which could be produced by air plasma spraying, a combination comprising a rough open-pored titanium coating and a HA top layer is also conceivable. The contacting park could be made of a self lubricated material such as a waxy polymer, such as PTFE, PFA, FEP, PE and UHMW PE, or a powder metallurgy material which could be infused with a lubricant, which preferably is a biocompatible lubricant such as a Hyaluronic acid derivate. It is also conceivable that the material of contacting parts or surfaces of the medical device herein is adapted to be constantly or intermittently lubricated. According to some embodiments the park or portions of the medical device could comprise a combination of metal materials and/or carbon fibers and/or boron, a combination of metal and plastic materials, a combination of metal and carbon based material, a combination of carbon and plastic based material, a combination of flexible and stiff materials, a combination of elastic and less elastic materials, Corian or acrylic polymers.

Please note that any embodiment or part of embodiment as well as any method or part of method could be combined in any way. All examples herein should be seen as part of the general description and therefore possible to combine in any way in general terms.

The invention claimed is:

1. A medical device for implantation in a hip joint of a patient, the hip joint having a caput femur integrated with a collum femur having a collum and caput center axis, extending longitudinally along the collum and caput femur, in the center thereof, wherein said medical device comprises:
    a) an elongated portion being connected to a prosthetic spherical portion adapted to replace the caput femur, and
    b) wherein said prosthetic spherical portion is adapted to be movably placed in a prosthetic replacement or the acetabulum, the prosthetic replacement for the acetabulum being fixated to the pelvic bone and having at least one extending portion for clasping said prosthetic spherical portion, wherein,
    i) said prosthetic spherical portion and elongated portion together are asymmetrically sized and formed for replacing the proximal portion of the femoral bone,
    ii) said elongated portion comprises a restricting portion adapted to restrict the motion range of the prosthetic replacement for the acetabulum in relation to said spherical portion, and wherein
    iii) said elongated portion comprising a receiving portion being placed frontal to the coronal pelvis plane for receiving a portion of said prosthetic artificial acetabulum, wherein said receiving portion makes the elongated portion rotationally asymmetric around the collum and caput center axis so that said restricting portion of said elongated portion is enables an advantageous motion range in relation to said prosthetic replacement for the acetabulum, when implanted and being in a defined base position.

2. The medical device according to claim 1, wherein said receiving portion is at least one recess adapted to receive a portion of said prosthetic artificial acetabulum, when implanted.

3. The medical device according to claim 2, wherein said recess is adapted to be placed frontal to the coronal pelvis plane, when implanted and being in a defined base position.

4. The medical device according to claim 2, wherein said recess is adapted to be placed in the frontal quadrant, when implanted and being in a defined base position.

5. The medical device according to claim 2, wherein said recess is adapted to be placed in the proximal quadrant, when implanted and being in a defined base position.

6. The medical device according to claim 2, wherein said recess is adapted to be placed in the distal quadrant, when implanted and being in a defined base position.

7. The medical device according to claim 2, wherein said recess is more than 2 mm deep.

8. The medical device according to claim 2, wherein said recess is more than 4 mm deep.

9. The medical device according to claim 2, wherein said recess is more than 6 mm deep.

10. The medical device according to claim 2, wherein said recess is more than 8 mm deep.

11. The medical device according to claim 1, wherein said elongated portion comprises an adaptation adapted to receive said extending portion when implanted.

12. The medical device according to claim 11, wherein said adaptation comprises a bent portion of said elongated portion, and wherein said bent portion is bent such that said restricting portion of said elongated portion mainly is placed in the dorsal quadrant, when implanted and being in a defined base position.

13. The medical device according to claim 1, wherein a cross-section of said restricting portion of said elongated portion, perpendicular to the caput and collum center axis, comprises a first distance and a second distance, wherein a center point of a line of said first distance intersects a center point of a line of said second distance, and wherein said first distance is shorter than said second distance.

14. The medical device according to claim 1, wherein said restricting portion of said elongated portion is adapted to be substantially aligned with said collum center axis and adapted to be eccentrically placed in relation to said collum axis, when implanted, and being in a defined base position.

15. The medical device according to claim 1, wherein a cross-section of the restricting portion of the elongated portion, perpendicular to the collum center axis, is at least one of: circular, polygonal and elliptical.

16. The medical device system according to claim 1, wherein the prosthetic concave replacement for the acetabulum is adapted to receive the spherical portion in connection with said medical device, wherein:
    a) an inner surface comprises an equator which is the largest circular circumference of an inner contacting surface, which is a surface adapted to be in contact with the spherical portion, and
    b) the at least one extending portion passes beyond the equator line, such that an end portion of the inner contacting surface of the inner surface forms a circular extension line having a smaller circumference than the equator line, and
    c) the at least one extending portion circumferentially extends discontinuously along the equator line, such that a portion of the medical device can be placed between the extension line and the equator line.

17. The medical device system according to claim 1, wherein two extending portions extends circumferentially along the equator line, in at least one of:
    a) the distal and proximal quadrant thereof,
    b) the proximal and dorsal quadrant thereof,
    c) the distal and dorsal quadrant thereof,
    d) the distal, dorsal and proximal quadrant thereof, when the prosthetic replacement for the acetabulum is placed in its final position.

18. The medical device according to claim 17, wherein the extending portion and the restricting portion of the elongated portion are adapted to be placed in relation to each other when implanted in the base position, such that at least one of:
    a) adduction is restricted more degrees than flexion,
    b) abduction is restricted more degrees than flexion,
    c) adduction is restricted more degrees than extension, and
    d) abduction is restricted more degrees than extension.

19. The medical device according to claim 1, wherein a major portion of said restricting portion of said elongated portion is adapted to be placed in the dorsal quadrant, when implanted, and being in a defined base position, such that extension is more restricted than flexion.

20. The medical device according to claim 1, wherein said at least one extending portion is configured to release said prosthetic spherical portion at a threshold strain in said hip joint.

* * * * *